(12) United States Patent
Gulati et al.

(10) Patent No.: US 9,766,126 B2
(45) Date of Patent: Sep. 19, 2017

(54) DYNAMIC RADIALLY CONTROLLED LIGHT INPUT TO A NONINVASIVE ANALYZER APPARATUS AND METHOD OF USE THEREOF

(71) Applicant: Zyomed Corp., Altadena, CA (US)

(72) Inventors: Sandeep Gulati, La Canada, CA (US); Thomas George, La Canada, CA (US); Timothy L. Ruchti, Gurnee, IL (US); Alan Abul-Haj, Mesa, AZ (US); Kevin H. Hazen, Gilbert, AZ (US)

(73) Assignee: Zyomed Corp., Altadena, CA (US)

( * ) Notice: Subject to any disclaimer, the term of this patent is extended or adjusted under 35 U.S.C. 154(b) by 793 days.

(21) Appl. No.: 13/941,389

(22) Filed: Jul. 12, 2013

(65) Prior Publication Data

US 2015/0015888 A1 Jan. 15, 2015

(51) Int. Cl.

| A61B 5/1455 | (2006.01) |
| G01J 3/42 | (2006.01) |
| G01N 21/47 | (2006.01) |
| A61B 5/00 | (2006.01) |
| A61B 5/107 | (2006.01) |
| A61B 5/145 | (2006.01) |

(52) U.S. Cl.
CPC ............ *G01J 3/42* (2013.01); *A61B 5/0022* (2013.01); *A61B 5/1079* (2013.01); *A61B 5/1455* (2013.01); *A61B 5/14552* (2013.01); *A61B 5/6801* (2013.01); *G01N 21/474* (2013.01); *A61B 5/14532* (2013.01); *G01N 2021/4742* (2013.01); *G01N 2021/4747* (2013.01); *G01N 2201/0826* (2013.01)

(58) Field of Classification Search
CPC . A61B 5/1455; A61B 5/14552; A61B 5/6801; A61B 5/6844; A61B 5/14532
See application file for complete search history.

(56) References Cited

U.S. PATENT DOCUMENTS 3,700,891 A 10/1972 Luft
4,583,545 A 4/1986 Towe
(Continued)

FOREIGN PATENT DOCUMENTS

WO WO2010/096081 A1 8/2010

OTHER PUBLICATIONS

Amerov et al. Method and device for non-invasive blood glucose measurement. 1999 Proc. Conf. Opt. Diag.Biol. Fluids IV SPIE 3599:33-42.
(Continued)

*Primary Examiner* — Eric Winakur
(74) *Attorney, Agent, or Firm* — Goodwin Procter LLP

(57) ABSTRACT

An analyzer apparatus and method of use thereof is described to dynamically irradiate a sample with incident light where the incident light is varied in time in terms of any of: position, radial position relative to a point of the skin of a subject, solid angle, incident angle, depth of focus, energy, and/or intensity. For example, the incident light is varied in radial position as a function of time relative to one or more of a sample site, a point on skin of the subject, a detection optic, and/or a sample volume observed by a detection system. The radially varied incident light is used to enhance and/or vary light probing the epidermis, the dermis, and/or the subcutaneous fat of the subject or of a group of subjects.

12 Claims, 11 Drawing Sheets

(56) References Cited

U.S. PATENT DOCUMENTS

| | | |
|---|---|---|
| 4,975,581 A | 12/1990 | Robinson et al. |
| 5,057,695 A | 10/1991 | Hirao |
| 5,086,229 A | 2/1992 | Rosenthal |
| 5,229,841 A | 7/1993 | Taranowski et al. |
| 5,237,178 A | 8/1993 | Rosenthal |
| 5,324,979 A | 6/1994 | Rosenthal |
| 5,459,317 A | 10/1995 | Small et al. |
| 5,492,118 A | 2/1996 | Gratton |
| 5,551,422 A | 9/1996 | Simonsen |
| 5,553,616 A | 9/1996 | Ham et al. |
| 5,636,633 A | 6/1997 | Messerschmidt et al. |
| 5,655,530 A | 8/1997 | Messerschmidt |
| 5,747,806 A | 5/1998 | Khalil et al. |
| 5,750,994 A | 5/1998 | Schlager |
| 5,823,951 A | 10/1998 | Messerschmidt |
| 5,945,676 A | 8/1999 | Khalil et al. |
| 5,957,841 A | 9/1999 | Maruo et al. |
| 6,016,435 A | 1/2000 | Maruo |
| 6,040,578 A | 3/2000 | Malin et al. |
| 6,061,582 A | 5/2000 | Small et al. |
| 6,067,463 A | 5/2000 | Jeng |
| 6,114,699 A | 9/2000 | Barton et al. |
| 6,115,065 A | 9/2000 | Yadid-Pecht |
| 6,115,673 A | 9/2000 | Malin et al. |
| 6,122,042 A | 9/2000 | Wunderman |
| 6,152,876 A | 11/2000 | Robinson et al. |
| 6,188,705 B1 | 2/2001 | Krainak |
| 6,236,047 B1 | 5/2001 | Malin et al. |
| 6,240,306 B1 | 5/2001 | Rohrscheib et al. |
| 6,263,221 B1 | 7/2001 | Chance |
| 6,280,381 B1 | 8/2001 | Malin et al. |
| 6,353,226 B1 | 3/2002 | Khalil et al. |
| 6,405,065 B1 | 6/2002 | Malin et al. |
| 6,411,373 B1 | 6/2002 | Garside et al. |
| 6,415,167 B1 | 7/2002 | Blank et al. |
| 6,442,408 B1 | 8/2002 | Wenzel et al. |
| 6,456,870 B1 | 9/2002 | Rennert et al. |
| 6,475,800 B1 | 11/2002 | Hazen et al. |
| 6,487,429 B2 | 11/2002 | Hockersmith et al. |
| 6,493,566 B1 | 12/2002 | Ruchti et al. |
| 6,501,982 B1 | 12/2002 | Ruchti et al. |
| 6,512,936 B1 | 1/2003 | Monfre et al. |
| 6,512,937 B2 | 1/2003 | Blank et al. |
| 6,518,558 B1 | 2/2003 | Bohm |
| 6,526,298 B1 | 2/2003 | Khalil |
| 6,534,012 B1 | 3/2003 | Hazen et al. |
| 6,571,117 B1 | 5/2003 | Marbach |
| 6,574,490 B2 | 6/2003 | Abbink et al. |
| 6,587,196 B1 | 7/2003 | Stippick et al. |
| 6,587,199 B1 | 7/2003 | Luu |
| 6,587,702 B1 | 7/2003 | Ruchti et al. |
| 6,594,513 B1 | 7/2003 | Jobsis |
| 6,615,061 B1 | 9/2003 | Khallil |
| 6,640,117 B2 | 10/2003 | Makarewicz et al. |
| 6,662,031 B1 | 12/2003 | Khalil |
| 6,668,181 B2 | 12/2003 | Wenzel et al. |
| 6,671,542 B2 | 12/2003 | Rennert et al. |
| 6,675,029 B2 | 1/2004 | Monfre et al. |
| 6,697,654 B2 | 2/2004 | Lorenz et al. |
| 6,704,662 B2 | 3/2004 | Gulati |
| 6,718,189 B2 | 4/2004 | Rohrscheib et al. |
| 6,728,560 B2 | 4/2004 | Kollias |
| 6,738,652 B2 | 5/2004 | Mattu et al. |
| 6,777,240 B2 | 8/2004 | Hazen et al. |
| 6,788,965 B2 | 9/2004 | Ruchti et al. |
| 6,816,241 B2 | 11/2004 | Grubisic |
| 6,839,584 B2 | 1/2005 | Makarewicz et al. |
| 6,844,994 B2 | 1/2005 | Melzer |
| 6,864,978 B1 | 3/2005 | Hazen et al. |
| 6,871,169 B1 | 3/2005 | Hazen et al. |
| 6,876,931 B2 | 4/2005 | Lorenz et al. |
| 6,956,649 B2 | 10/2005 | Acosta et al. |
| 6,990,364 B2 | 1/2006 | Ruchti et al. |
| 6,998,247 B2 | 2/2006 | Monfre et al. |
| 7,009,180 B2 | 3/2006 | Sterling |
| 7,010,336 B2 | 3/2006 | Lorenz et al. |
| 7,015,782 B2 | 3/2006 | Kincaid et al. |
| 7,038,774 B2 | 5/2006 | Hazen et al. |
| 7,039,446 B2 | 5/2006 | Ruchti et al. |
| 7,072,700 B2 * | 7/2006 | Yamamoto ......... A61B 5/14553 600/310 |
| D526,719 S | 8/2006 | Richie, Jr. et al. |
| D529,616 S | 10/2006 | Deros et al. |
| 7,133,710 B2 | 11/2006 | Acosta et al. |
| 7,147,153 B2 | 12/2006 | Rowe et al. |
| 7,183,102 B2 | 2/2007 | Monfre et al. |
| 7,206,623 B2 | 4/2007 | Blank et al. |
| 7,233,816 B2 | 6/2007 | Blank et al. |
| 7,299,079 B2 | 11/2007 | Rebec |
| 7,299,080 B2 | 11/2007 | Acosta et al. |
| 7,317,938 B2 | 1/2008 | Lorenz et al. |
| 7,333,843 B2 | 2/2008 | Monfre et al. |
| 7,356,364 B1 | 4/2008 | Bullock et al. |
| 7,383,069 B2 | 6/2008 | Ruchti et al. |
| 7,395,158 B2 | 7/2008 | Monfre et al. |
| 7,436,511 B2 | 10/2008 | Ruchti et al. |
| 7,440,786 B2 | 10/2008 | Hockersmith et al. |
| 7,488,930 B2 | 2/2009 | Ajgaonkar |
| 7,505,801 B2 | 3/2009 | Monfre et al. |
| 7,508,524 B2 | 3/2009 | Mahadevan-Jansen |
| 7,509,153 B2 | 3/2009 | Blank et al. |
| 7,519,406 B2 | 4/2009 | Blank et al. |
| 7,567,876 B2 | 7/2009 | Gulati |
| 7,571,056 B2 | 8/2009 | Ben-Menahem et al. |
| 7,593,230 B2 | 9/2009 | Abul-Haj et al. |
| 7,606,608 B2 | 10/2009 | Blank et al. |
| 7,620,212 B1 | 11/2009 | Allen et al. |
| 7,620,674 B2 | 11/2009 | Ruchti et al. |
| 7,640,140 B2 | 12/2009 | Ruchti et al. |
| 7,697,966 B2 | 4/2010 | Monfre et al. |
| 7,698,105 B2 | 4/2010 | Ruchti et al. |
| RE41,333 E | 5/2010 | Blank et al. |
| 7,738,085 B2 | 6/2010 | Braig |
| 7,751,192 B2 | 7/2010 | Abul-Haj et al. |
| 7,751,594 B2 | 7/2010 | Rowe et al. |
| 7,787,924 B2 | 8/2010 | Acosta et al. |
| 7,872,734 B2 | 1/2011 | Braig |
| 8,082,015 B2 | 12/2011 | Yodh et al. |
| 8,109,634 B2 | 2/2012 | Gil |
| 8,160,666 B2 | 4/2012 | Rebec |
| 8,170,326 B2 | 5/2012 | Gulati et al. |
| 8,175,665 B2 | 5/2012 | Baker et al. |
| 8,190,241 B2 | 5/2012 | Ntziachristos |
| 8,285,010 B2 | 10/2012 | Rowe |
| 8,315,681 B2 | 11/2012 | Kanayama et al. |
| 8,346,327 B2 | 1/2013 | Campbell |
| 8,380,268 B2 | 2/2013 | Georgakoudi |
| 8,712,504 B2 | 4/2014 | Godavarty |
| 2002/0026106 A1 | 2/2002 | Khalil et al. |
| 2002/0041166 A1 | 4/2002 | Grubisic |
| 2002/0042558 A1 | 4/2002 | Mendelson |
| 2002/0049389 A1 | 4/2002 | Abreu |
| 2002/0084417 A1 | 7/2002 | Khalil |
| 2003/0060693 A1 | 3/2003 | Monfre |
| 2003/0078504 A1 | 4/2003 | Rowe |
| 2003/0086074 A1 | 5/2003 | Braig et al. |
| 2003/0139667 A1 | 7/2003 | Hewko |
| 2003/0166997 A1 | 9/2003 | Chance |
| 2003/0208113 A1 | 11/2003 | Mault |
| 2003/0223532 A1 | 12/2003 | Clinthorne |
| 2004/0132168 A1 | 7/2004 | Rule |
| 2004/0162470 A1 | 8/2004 | Tu |
| 2004/0246490 A1 | 12/2004 | Wang |
| 2005/0010090 A1 | 1/2005 | Acosta et al. |
| 2005/0020892 A1 | 1/2005 | Acosta |
| 2005/0033127 A1 | 2/2005 | Ciurczak et al. |
| 2005/0054908 A1 | 3/2005 | Blank et al. |
| 2005/0124869 A1 | 6/2005 | Hefti et al. |
| 2005/0187439 A1 | 8/2005 | Blank |
| 2005/0261560 A1 | 11/2005 | Ridder |
| 2005/0267342 A1 | 12/2005 | Blank |
| 2006/0116562 A1 | 6/2006 | Acosta et al. |
| 2006/0157640 A1 | 7/2006 | Perlman |
| 2006/0173254 A1 | 8/2006 | Acosta et al. |

(56) References Cited

U.S. PATENT DOCUMENTS

| | | |
|---|---|---|
| 2006/0173255 A1 | 8/2006 | Acosta et al. |
| 2006/0183983 A1 | 8/2006 | Acosta et al. |
| 2006/0195023 A1 | 8/2006 | Acosta et al. |
| 2006/0200017 A1 | 9/2006 | Monfre |
| 2006/0206018 A1 | 9/2006 | Abul-Haj |
| 2006/0211927 A1 | 9/2006 | Acosta et al. |
| 2006/0234386 A1 | 10/2006 | Burns |
| 2006/0247536 A1 | 11/2006 | Koski |
| 2007/0106172 A1 | 5/2007 | Abreu |
| 2007/0149868 A1 | 6/2007 | Blank et al. |
| 2007/0161876 A1 | 7/2007 | Bambot |
| 2007/0167704 A1 | 7/2007 | Chance |
| 2007/0255141 A1 | 11/2007 | Esenaliev |
| 2007/0278389 A1 | 12/2007 | Ajgaonkar |
| 2008/0076985 A1 | 3/2008 | Matousek |
| 2008/0135780 A1 | 6/2008 | Giering |
| 2008/0221410 A1 | 9/2008 | Campbell |
| 2008/0232653 A1 | 9/2008 | Rowe |
| 2008/0291394 A1 | 11/2008 | Ishak |
| 2008/0306363 A1 | 12/2008 | Chaiken et al. |
| 2008/0319286 A1 | 12/2008 | Ridder |
| 2009/0003764 A1 | 1/2009 | Ridder |
| 2009/0043178 A1 | 2/2009 | Belotserkovsky |
| 2009/0098587 A1 | 4/2009 | Hetzel et al. |
| 2009/0185191 A1 | 7/2009 | Boppart |
| 2009/0225277 A1 | 9/2009 | Gil |
| 2009/0247840 A1 | 10/2009 | Blank et al. |
| 2009/0275841 A1 | 11/2009 | Melendez |
| 2010/0010325 A1 | 1/2010 | Ridder |
| 2010/0016689 A1 | 1/2010 | Kanayama et al. |
| 2010/0113899 A1 | 5/2010 | Robinson et al. |
| 2010/0145200 A1 | 6/2010 | Mahadevan-Jansen |
| 2010/0160747 A1 | 6/2010 | Robinson et al. |
| 2011/0077496 A1 | 3/2011 | Chaiken |
| 2011/0184260 A1 | 7/2011 | Robinson |
| 2012/0057164 A1 | 3/2012 | Tezuka |
| 2012/0059232 A1 | 3/2012 | Gross |
| 2012/0129269 A1 | 5/2012 | Choi |
| 2012/0130215 A1 | 5/2012 | Fine |
| 2013/0261413 A1 | 10/2013 | Kawahara et al. |
| 2015/0011849 A1 | 1/2015 | Ruchti |
| 2015/0011850 A1 | 1/2015 | Ruchti |
| 2015/0015888 A1 | 1/2015 | Gulati |
| 2015/0018642 A1 | 1/2015 | Gulati |
| 2015/0018644 A1 | 1/2015 | Gulati |
| 2015/0018646 A1 | 1/2015 | Gulati |
| 2015/0041656 A1 | 2/2015 | Novotny |
| 2015/0045636 A1 | 2/2015 | Novotny |

OTHER PUBLICATIONS

Arnold, Mark A.; Small, Gary W.; Anal. Chem. 1990, 62, 1457-1464.

Bykov et al. Monte Carlo Simulation of Light Propagation in human tissues and Noninvasive Glucos Sensing. 2008 in "Handbook of Optical Sensing of Glucose in Biological Fluids and Tissues" Tuchin Edt., Taylor&Francis, Chap.3 p. 65-95.

Chaiken et al. Analyzing near-infrared scattering from human skin to monitor changes in hematocrit. 2011 J.Biomed.Optics 16:097005-1-097005-18.

Delpy et al. Estimation of optical pathlength through tissue from direct time of flight measurement. 1988 Phys.Med.Biol. 33:1433-1442.

Durduran et al. 2010 Rep. Prog. Phys. 73:076701-1 43 pages.

Farrell et al. A Diffusion theory model of spatially resolved steady-state diffuse reflectance for the noninvasive determination of tissue optical properties. 1992 Am. Assoc. Phys. Med. 19:879-888.

Flock et al. Monte-Carlo modeling of light propagation in highly scattering tissues II. Comparison with measurements in phantoms. 1989 IEEE Trans Biomeda Engina 36:1169-1173.

Haaland David M.; Robinson, Ries M.; Koepp, Gary W.; Thomas, Edward V.; Eaton, Philip R. Appl. Spect. 1992, 46, 1575-1578.

Hazen, Kevin H.; Arnold, Mark A.; Small, Gary W.; Anal. Chem. 1990, 48, 477-483.

Kirillin et al. Application of time gating in the measurement of glucose level in a three-layer biotissue model by using ultrashort laser pulses. 2008 Quantum Electronics 38:486-490.

Larsson et al. In vivo determination of local skin optical properties and photon path length by use of spatially resolved diffuse reflectance with applications in laser Doppler flowmetry. 2003 Applied Optics 42:124-134.

Liu et al. Next step of non-invasive glucose monitor by NIR technique from the well controlled measuring condition and results. 2006 Opt.Quant.Electro. 37:1305-1317.

Marquardt, L.A.; Arnold, M.A.; Small, Gary W. Anal. Chem 1993, 65, 3271-3278.

Nayar et al., "High dynamic range imagine: spatially varying pixel exposures", 2000, IEEE Conference on Computer Vision and Pattern Recognition (1), pp. 472-479.

Noda. Recent advancement in the field of two-dimensional correlation spectroscopy. 2008 J.Mol.Struct. 883-884:2-26.

Small, Gary W.; Arnold, M.A.; Marquardt, Lois A. Anal. Chem. 1993, 65, 3279-3289.

Small, Gary W.; Arnold, Mark A.; Marquardt, Lois A.; Anal. Chem. 1993, 65, 3279-3289.

Tearney et al. Scanning single-mode fiber optic catheter-endoscope for optical coherence tomography. 1996 Optics Let. 21:543-545.

Thilwind et al. Improved depth resolution in near-infrared diffuse reflectance spectroscopy using obliquely oriented fibers. 2009 J.Biomed.Optics 14:024026-1-024026-9.

Xu et al. The interface between probe and skin in non-invasive glucose sensing. 2003 Proc. SPIE 5068:104-111.

Yen et al. Calculated Calibration Models for Glucose in Cutaneous Tissue From Temperature Modulation of Localized Reflectance Measurements. 2004 Proc. SPIE 5771:166-173.

\* cited by examiner

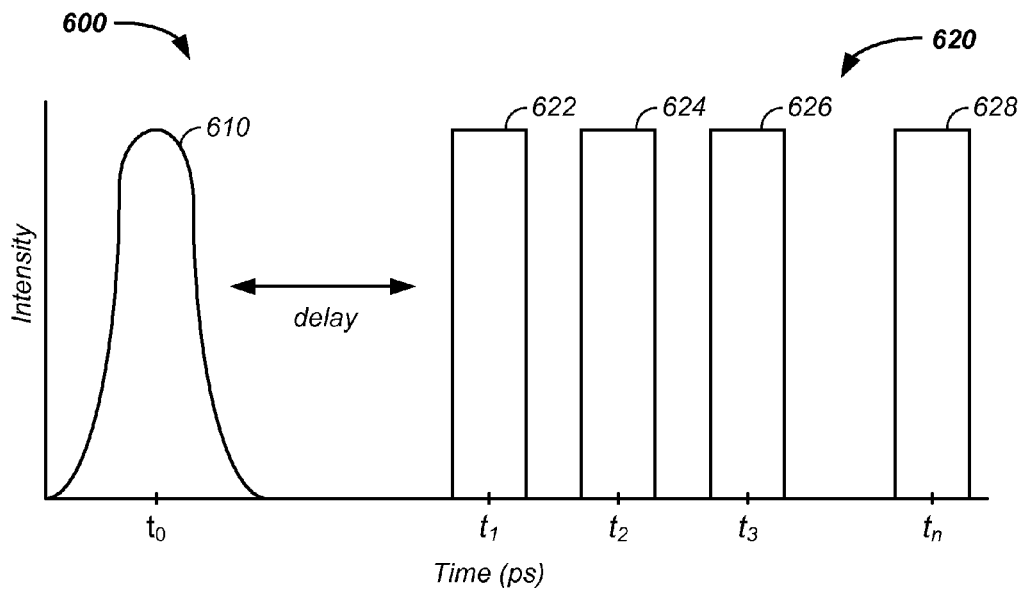
FIG. 6A
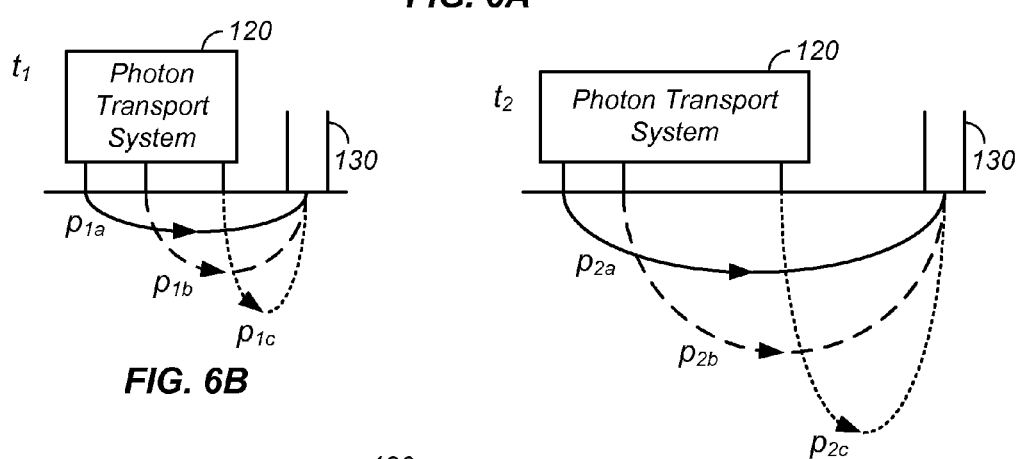
FIG. 6B
FIG. 6C
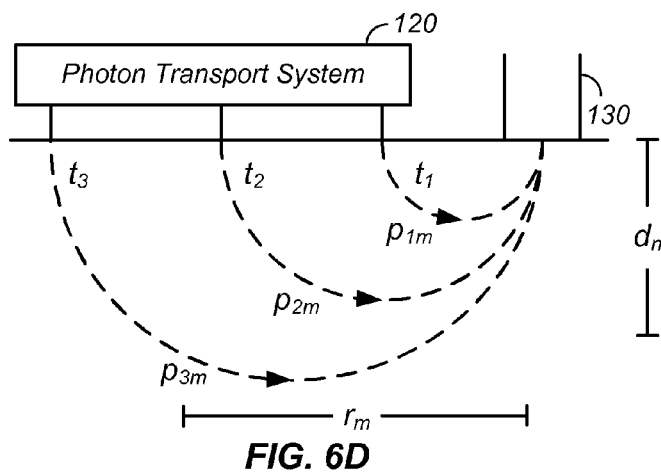
FIG. 6D

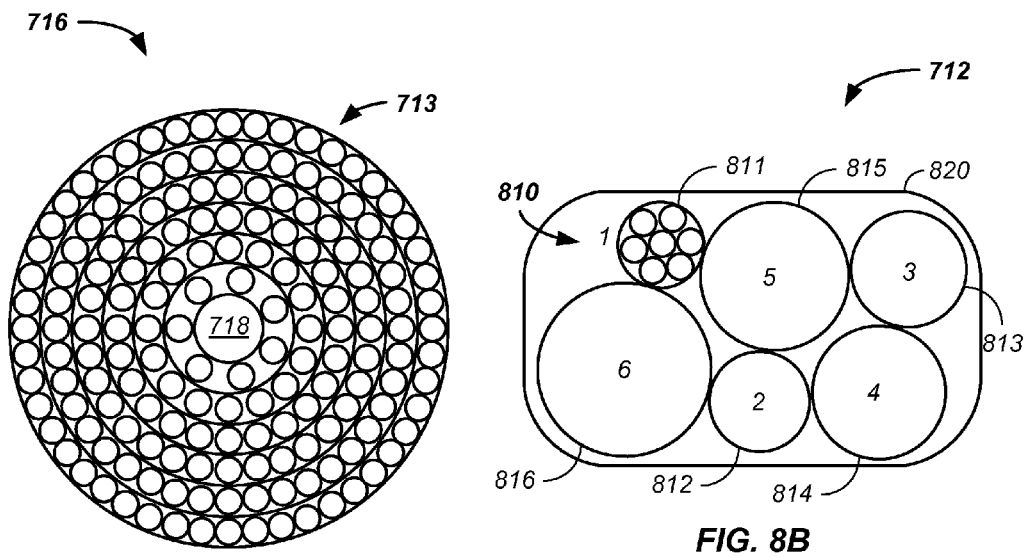
FIG. 8A
FIG. 8B
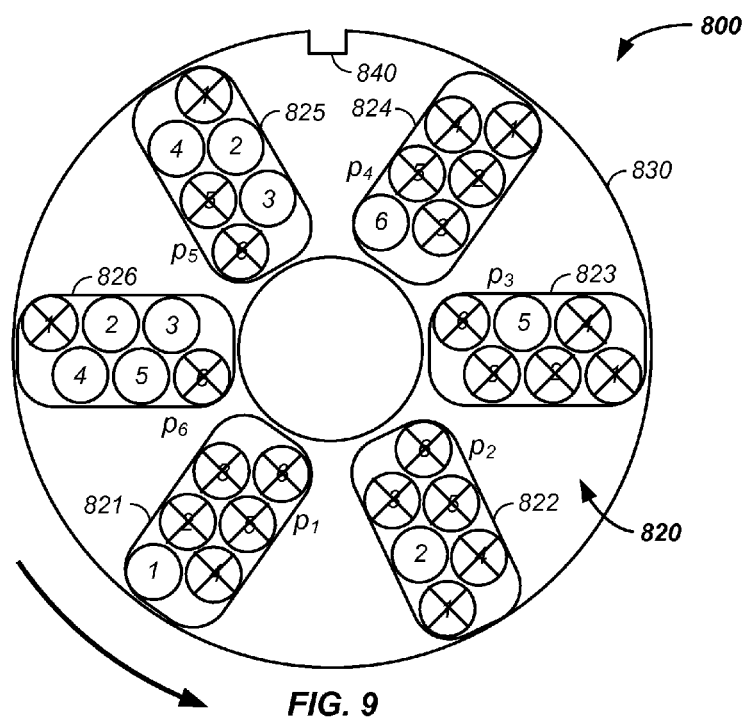
FIG. 9

DYNAMIC RADIALLY CONTROLLED LIGHT INPUT TO A NONINVASIVE ANALYZER APPARATUS AND METHOD OF USE THEREOF

CROSS REFERENCES TO RELATED APPLICATIONS

This application is a continuation-in-part of U.S. patent application Ser. No. 13/941,369 filed Jul. 12, 2013, which claims the benefit of:
U.S. provisional patent application No. 61/672,195 filed Jul. 16, 2012;
U.S. provisional patent application No. 61/700,291 filed Sep. 12, 2012; and
U.S. provisional patent application No. 61/700,294 filed Sep. 12, 2012,
all of which are incorporated herein in their entirety by this reference thereto.

TECHNICAL FIELD OF THE INVENTION

The present invention relates to a noninvasive analyzer with control of irradiation radius relative to a detection zone for use in analyte concentration estimation.

DESCRIPTION OF THE RELATED ART

Patents and literature related to the current invention are summarized herein.

Diabetes

Diabetes mellitus or diabetes is a chronic disease resulting in the improper production and/or use of insulin, a hormone that facilitates glucose uptake into cells. Diabetes is broadly categorized into four forms grouped by glucose concentration state: hyperinsulinemia (hypoglycemia), normal physiology, impaired glucose tolerance, and hypoinsulinemia (hyperglycemia).

Diabetics have increased risk in three broad categories: cardiovascular heart disease, retinopathy, and/or neuropathy. Complications of diabetes include: heart disease, stroke, high blood pressure, kidney disease, nerve disease and related amputations, retinopathy, diabetic ketoacidosis, skin conditions, gum disease, impotence, and/or fetal complications.

Diabetes is a common and increasingly prevalent disease. Currently, diabetes is a leading cause of death and disability worldwide. The World Health Organization estimates that the number of people with diabetes will grow to three hundred million by the year 2025.

Long term clinical studies show that the onset of diabetes related complications is significantly reduced through proper control of blood glucose concentrations, The Diabetes Control and Complications Trial Research Group, "The Effect of Intensive Treatment of Diabetes on the Development and Progression of Long-Term Complications in Insulin-Dependent Diabetes Mellitus", N. Eng. J. of Med., 1993, vol. 329, pp. 977-986.

Fiber Optic Sample Bundle

Garside, J.; et. al., "Fiber Optic Illumination and Detection Patterns, Shapes, and Locations for use in Spectroscopic Analysis", U.S. Pat. No. 6,411,373 (Jun. 25, 2002) describe software and algorithms to design fiber optic excitation and/or collection patterns in a sample probe.

Maruo, K. et. al., "Device for Non-Invasive Determination of Glucose Concentration in Blood", European patent application no. EP 0843986 B1 (Mar. 24, 2004) described the use of light projecting fiber optics in the range of 0.1 to 2 millimeters from light receiving fiber optics at the contacted fiber optic bundle/sample interface.

Problem Statement

What is needed is a noninvasive glucose concentration analyzer having precision and accuracy suitable for treatment of diabetes mellitus.

SUMMARY OF THE INVENTION

The invention comprises a noninvasive analyzer apparatus having dynamic control of distance between a plurality of irradiation zones and a detection zone and a method of use thereof.

BRIEF DESCRIPTION OF THE DRAWINGS

A more complete understanding of the present invention is derived by referring to the detailed description and claims when considered in connection with the Figures, wherein like reference numbers refer to similar items throughout the Figures.

FIGS. 6(A-D) illustrate temporal resolution gating, FIG. 6A; probabilistic optical paths for a first elapsed time, FIG. 6B; probabilistic optical paths for a second elapsed time, FIG. 6C; and a temporal distribution method, FIG. 6D;
FIG. 8A illustrates a third example sample interface end of the fiber optic bundle and FIG. 8B illustrates a mask;
FIG. 9 illustrates a mask selection wheel.

Figure 1:
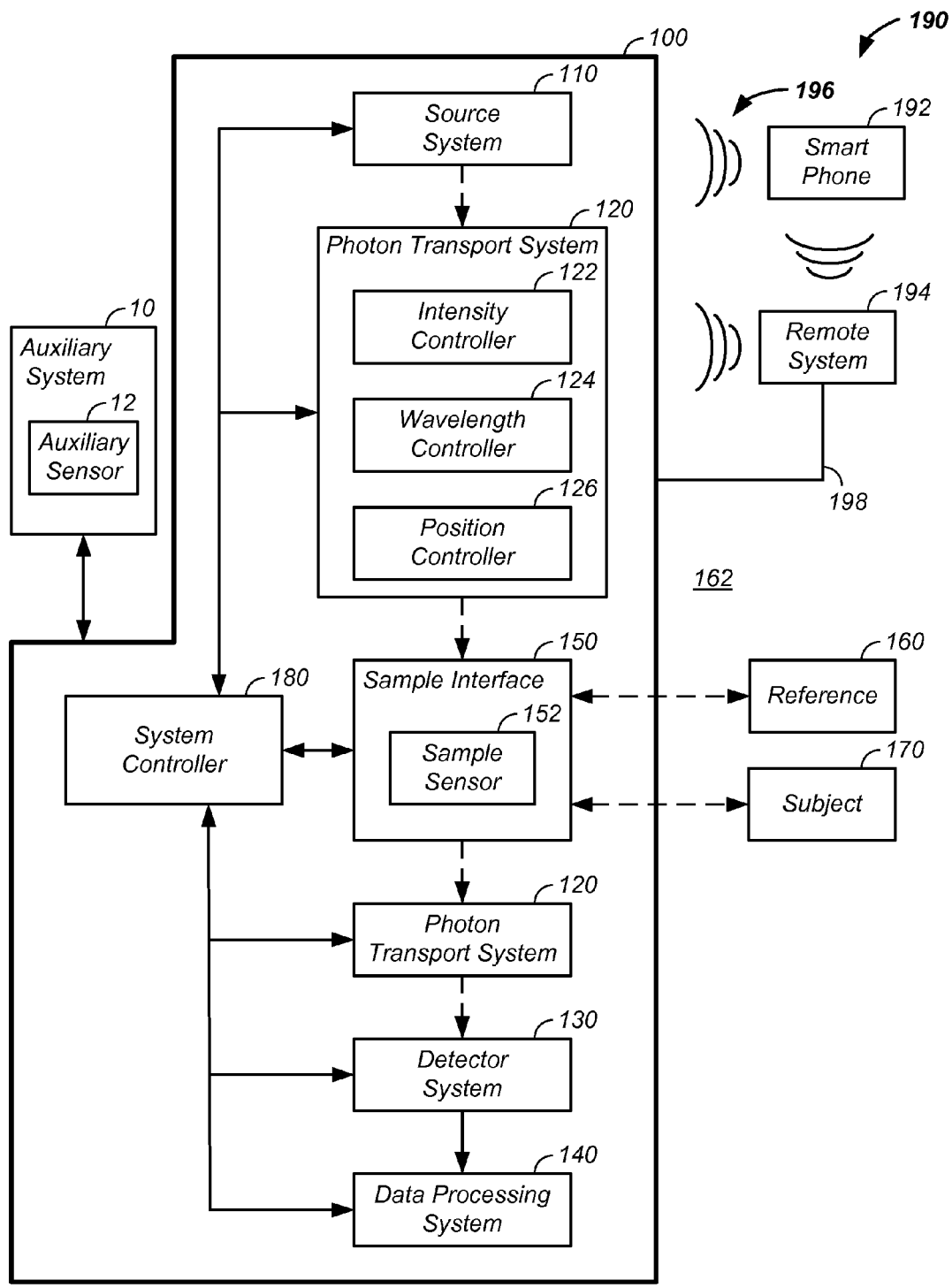
FIG. 1 illustrates an analyzer.

Elements and steps in the figures are illustrated for simplicity and clarity and have not necessarily been rendered according to any particular sequence. For example, steps that are performed concurrently or in a different order are illustrated in the figures to help improve understanding of embodiments of the present invention.

DETAILED DESCRIPTION OF THE PREFERRED EMBODIMENTS

The invention comprises an noninvasive apparatus configured for dynamic radial control of incident light position, angle, and/or solid angle relative to a detection zone and method of use thereof.

In another embodiment, a data processing system analyzes data from an analyzer to estimate and/or determine an analyte property, such as concentration using multiple types of data, such as from an external sensor, from two or more radial positions, and/or with two of more focusing depths.

In still another embodiment, an analyzer using light interrogates the sample using one or more of:
- a spatially resolved system;
  - a an incident light radial distance resolved system;
  - a controllable and variable incident light solid angle system; and
  - a controllable and variable incident light angle system;
- a time resolved system, where the times are greater than about 1, 10, 100, or 1000 microseconds;
- a picosecond timeframe resolved system, where times are less than about 1, 10, 100, or 1000 nanoseconds;
- an incident angle resolved system; and
- a collection angle resolved system.

Data from the analyzer is analyzed using a data processing system capable of using the information inherent in the resolved system data.

In yet another embodiment, a data processing system uses interrelationships of chemistry based a-priori spectral information related to absorbance of a sample constituent and/or the effect of the environment, such as temperature, on the spectral information.

In yet still another embodiment, a data processing system uses a first mapping phase to set instrument control parameters for a particular subject, set of subjects, and/or class of subjects. Subsequently, the control parameters are used in a second data collection phase to collect spectra of the particular subject or class of subjects.

In still yet another embodiment, a data processing system uses information related to contact pressure on a tissue sample site.

In another embodiment, a data processing system uses a combination of any of:
- spatially resolved information;
- temporally resolved information on a time scale of longer than about one microsecond;
- temporally resolved information on a sub one hundred picosecond timeframe;
- incident photon angle information;
- photon collection angle information;
- interrelationships of spectral absorbance and/or intensity information;
- environmental information;
- temperature information; and
- information related to contact pressure on a tissue sample site.

In still yet another embodiment, a temporal resolution gating noninvasive analyzer is used to determine an analyte property of a biomedical sample, such as a glucose concentration of a subject using light in the near-infrared region from 1000 to 2500 nanometers.

Axes

Herein, axes systems are separately defined for an analyzer and for an interface of the analyzer to a patient, where the patient is alternatively referred to as a subject.

Herein, when referring to the analyzer, an x, y, z-axes analyzer coordinate system is defined relative to the analyzer. The x-axis is the in the direction of the mean optical path. The y-axis crosses the mean optical path perpendicular to the x-axis. When the optical path is horizontal, the x-axis and y-axis define a x/y horizontal plane. The z-axis is normal to the x/y plane. When the optical path is moving horizontally, the z-axis is aligned with gravity, which is normal to the x/y horizontal plane. Hence, the x, y, z-analyzer coordinate system is defined separately for each optical path element. If necessary, where the mean optical path is not horizontal, the optical system is further defined to remove ambiguity.

Herein, when referring to the patient, an x, y, z-axes patient coordinate system is defined relative to a body part interfaced to the analyzer. Hence, the x, y, z-axes body coordinate system moves with movement of the body part. The x-axis is defined along the length of the body part, the y-axis is defined across the body part. As an illustrative example, if the analyzer interfaces to the forearm of the patient, then the x-axis runs longitudinally between the elbow and the wrist of the forearm and the y-axis runs across the forearm. Together, the x,y plane tangentially touches the skin surface at a central point of the interface of the analyzer to the body part, which is referred to as the center of the sample site, sample region, or sample site. The z-axis is defined as orthogonal to the x,y plane. Rotation of an object is further used to define the orientation of the object to the sample site. For example, in some cases a sample probe of the analyzer is rotatable relative to the sample site. Tilt refers to an off z-axis alignment, such as an off z-axis alignment of a probe of the analyzer relative to the sample site.

Analyzer

Referring now to FIG. 1, an analyzer 100 is illustrated. The analyzer comprises at least: a light source system 110, a photon transport system 120, a detector system 130, and a data processing system 140. In use the analyzer 100 estimates and/or determines a physical property, a sample state, a constituent property, and/or a concentration of an analyte.

Patient/Reference

Still referring to FIG. 1, an example of the analyzer 100 is presented. In this example, the analyzer 100 includes a sample interface 150, which interfaces to a reference material 160 and/or to a subject 170. Herein, for clarity of presentation a subject 170 in the examples is representative of a person, animal, a prepared sample, and/or patient. In practice, the analyzer 100 is used by a user to analyze the user, referred to as a subject 170, and is used by a medical professional to analyze a patient.

Controller

Still referring to FIG. 1, the analyzer 100 optionally includes a system controller 180. The system controller 180 is used to control one or more of: the light source system 110 or a light source 112 thereof, the photon transport system 120, the detector system 130 or a detector 132 thereof, the sample interface 150, position of the reference 160 relative to the sample interface 150, position of the subject 170 relative to the sample interface 150, and communication to an outside system 190, such as a smart phone 192, and/or a remote system 194 using a wireless communication system 196 and/or hard wired communication system 198. For example, the remote system includes a data processing system, a data storage system, and/or a data organization system.

Still referring to FIG. 1, the optional system controller 180 operates in any of a predetermined manner or in communication with the data processing system 140. In the case of operation in communication with the data processing system 140, the controller generates control statements using data and/or information about the current state of the analyzer 100, current state of a surrounding environment 162 outside of the analyzer 100, information generated by the data processing system 140, and/or input from a sensor, such as a sample interface sensor 152 or an auxiliary system 10 or an auxiliary sensor 12 thereof. Herein, the auxiliary system 10 is any system providing input to the analyzer 100.

Still referring to FIG. 1, the optional system controller 180 is used to control: photon intensity of photons from the source using an intensity controller 122, wavelength distribution of photons from the source 110 using a wavelength controller 124, and/or physical routing of photons from the source 110 using a position controller 126.

Still referring to FIG. 1, for clarity of presentation the optional outside system 190 is illustrated as using a smart phone 192. However, the smart phone 192 is optionally a cell phone, a tablet computer, a computer network, and/or a personal computer. Similarly, the smart phone 192 also refers to a feature phone, a mobile phone, a portable phone, and/or a cell phone. Generally, the smart phone 192 includes hardware, software, and/or communication features carried by an individual that is optionally used to offload requirements of the analyzer 100. For example, the smart phone 192 includes a user interface system, a memory system, a communication system, and/or a global positioning system. Further, the smart phone 192 is optionally used to link to the remote system 194, such as a data processing system, a medical system, and/or an emergency system. In another example at least one calculation of the analyzer in noninvasively determining a glucose concentration of the subject 170 is performed using the smart phone 192. In yet another example, the analyzer gathers information from at least one auxiliary sensor 12 and relays that information and/or a processed form of that information to the smart phone 192, where the auxiliary sensor is not integrated into the analyzer 100.

Source

Herein, the source system 110 generates photons in any of the visible, infrared, near-infrared, mid-infrared, and/or far-infrared spectral regions. In one case, the source system generates photons in the near-infrared region from 1100 to 2500 nm or any range therein, such as within the range of about 1200 to 1800 nm; at wavelength longer than any of 800, 900, 1000, and 1100 nm; and/or at wavelengths shorter than any of 2600, 2500, 2000, or 1900 nm.

Photon/Skin Interaction

Light interacts with skin through laws of physics to scatter and transmit through skin voxels.

Figure 2:
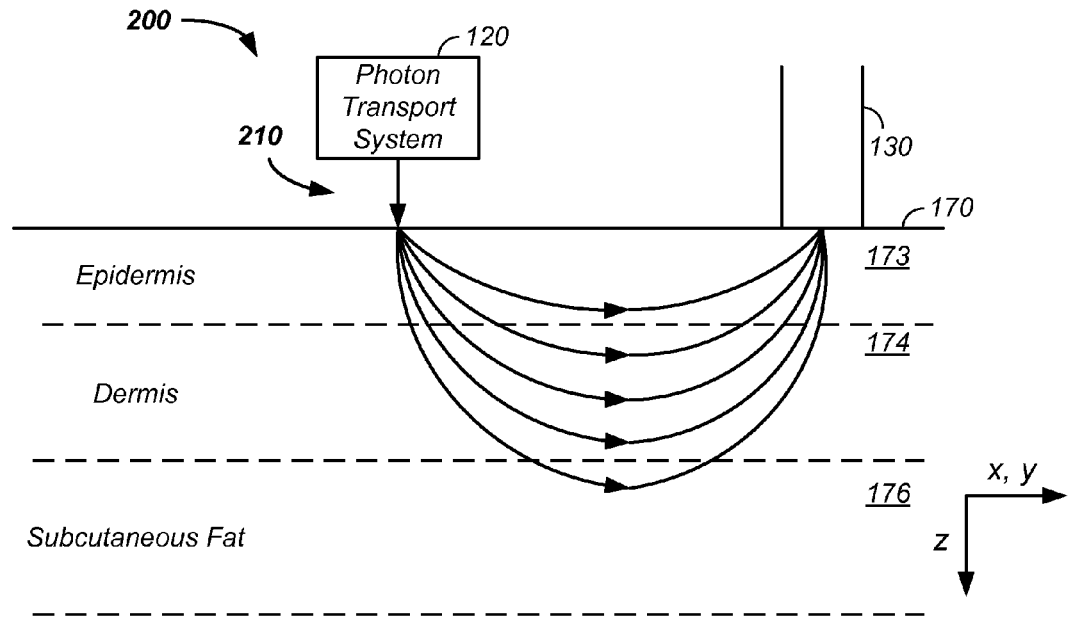
FIG. 2 illustrates diffusely reflecting optical paths.

Referring now to FIG. 2, for clarity of presentation and without limitation, in several examples provided herein a simplifying and non-limiting assumption is made, for some wavelengths, for some temperatures, and for some optical configurations, that a mean photon depth of penetration increases with mean radial distance between a photon illumination zone and a photon detection zone. For example, for photons transmitting from a sample illumination zone, through the subject, and through a photon detection zone, such as at a subject/analyzer interface:

at a first radial distance, photons penetrate with a mean maximum depth of penetration into an epidermal layer of a subject;
at a second larger radial distance, photons penetrate with a mean maximum depth of penetration into a dermal layer of the subject; and
at a third still larger radial distance, photons penetrate with a mean maximum depth of penetration into a subcutaneous fat layer of the subject.

Referring still to FIG. 2, a photon transit system 200 through skin layers of the subject 170 is illustrated. In this example, the photon transport system 120 guides light from a source 112 of the source system 110 to the subject 170. Further, in this example, the photon transport system 120 irradiates skin of the subject 170 over a narrow illumination zone, such as having an area of less than about 9, 4, 1, or ¼ mm$^2$. Optionally, the photons are delivered to the skin of the subject 170 through an optic proximately contacting, but not actually contacting, the skin, such as within about 0.5, 1.0, or 2.0 millimeters of the skin. The optional spatial gap 210 between the last input optic and skin of the subject is preferably small, such as less than about 0.1, 0.2, 0.5, or 1 millimeter or is large, such as greater than 1, 2, 3, 5, or 10 millimeters. Optionally, the distance between the analyzer and the skin of the subject 170 is maintained with a vibration and/or shake reduction system, such as is used in a vibration reduction camera or lens. For clarity of presentation, the photons are depicted as entering the skin at a single point. A portion of the photons traverse, or more particularly traverse through, the skin to a detection zone. The detection zone is a region of the skin surface where the detector system 130 gathers the traversing or diffusely reflected photons. Various photons traversing or diffusely scattering through the skin encounter an epidermis 173 or epidermis layer, a dermis 174 or dermis layer, and subcutaneous fat 176 or a subcutaneous fat layer. As depicted in FIG. 2, the diffuse reflectance of the various photons through the skin detected by the detection system 130 follow a variety of optical paths through the tissue, such as shallow paths through the epidermis 173, deeper paths through the epidermis 173 and dermis 174, and still deeper paths through the epidermis 173, dermis 174, and subcutaneous fat 176. However, for a large number of photons, there exists a mean photon path for photons from entering the skin that are detected by the detection system 130.

Pathlength

Herein, for clarity, without loss of generality, and without limitation, Beer's Law is used to described photon interaction with skin, though those skilled in the art understand deviation from Beer's Law result from sample scattering, index of refraction variation, inhomogeneity, turbidity, and/or absorbance out of a linear range of the analyzer 100.

Beer's Law, equation 1, states that:

$$A \alpha bC \qquad (\text{eq. 1})$$

where A is absorbance, b is pathlength, and C is concentration. Typically, spectral absorbance is used to determine concentration. However, the absorbance is additionally related to pathlength. Hence, determination of the optical pathlength traveled by the photons is useful in reducing error in the determined concentration. Two methods, described infra, are optionally used to estimate pathlength: (1) spatial resolution of pathlength and (2) temporal resolution of pathlength.

Algorithm

The data and/or derived information from each of the spatial resolution method and temporal resolution method are each usable with the data processing system 140. Examples provide, infra, illustrate: (1) both cases of the spatial resolution method and (2) the temporal resolution method. However, for clarity of presentation and without limitation, the photons in most examples are depicted as radially traversing from a range of input zones to a detection zone. Similarly, photons are optionally delivered, simultaneously and/or as a function of time, from an input zone to a range of detection zones. Still further, photons are optionally directed to a series of input zones, as a function of time, and one or more detection zones are used to detect the photons directed to the series of input zones, simultaneously and/or as a function of time.

Spatial Resolution

The first method of spatial resolution contains two cases. Herein, in a first case photons are depicted traversing from a range of input points on the skin to a radially located detector to derive photon interrogated sample path and/or depth information. However, in a second case, similar systems optionally use a single input zone of the photons to the skin and a plurality of radially located detector zones to determine optical sample photons paths and/or depth information. Still further, a combination of the first two cases, such as multiple sources and multiple detectors, is optionally used to derive photon path information in the skin.

Figure 3:
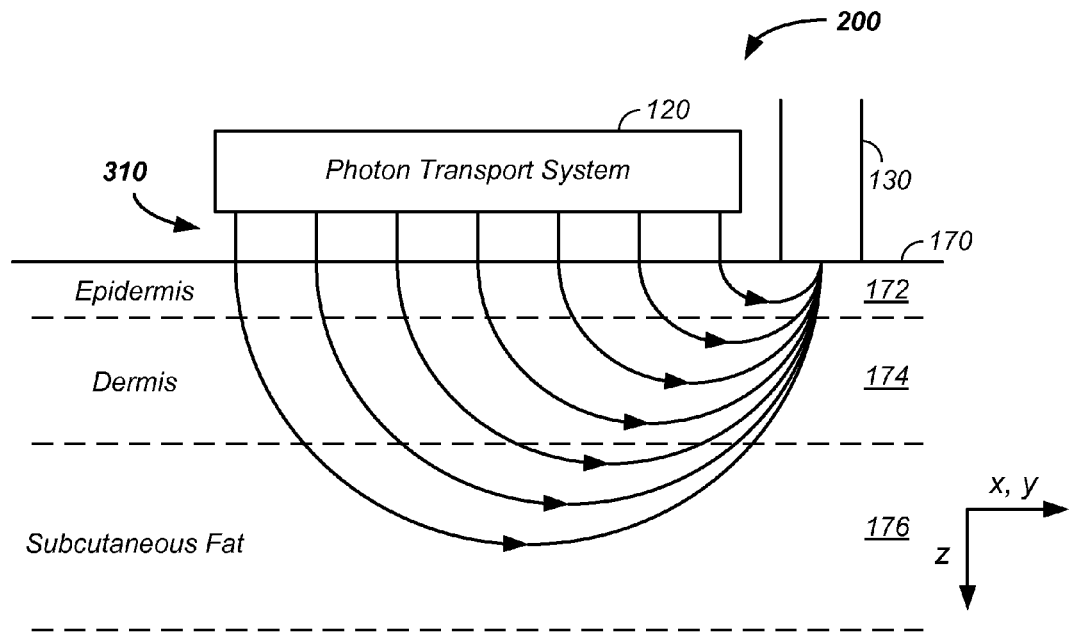
FIG. 3 illustrates probing tissue layers using a spatial distribution method.

In the first system, Referring now to FIG. 3, the photon transit system 200 of FIG. 2 is illustrated where the photon transport system 110 irradiates the skin of the subject 170 over a wide range of radial distance from the detection zone, such as at least about 0.1, 0.2, 0.3, 0.4, or 0.5 millimeters from the detection zone to less than about 1.0, 1.2, 1.4, 1.6, or 1.8 millimeters from the detection zone. In this example, a mean photon path is provided as a function of radial distance from the illumination zone to the detection zone. Generally, over a range of about zero to less than about two millimeters from the detection zone, the mean optical path of the detected diffusely scattering photons increases in depth for photons in the near-infrared traveling through skin.

Figure 4:
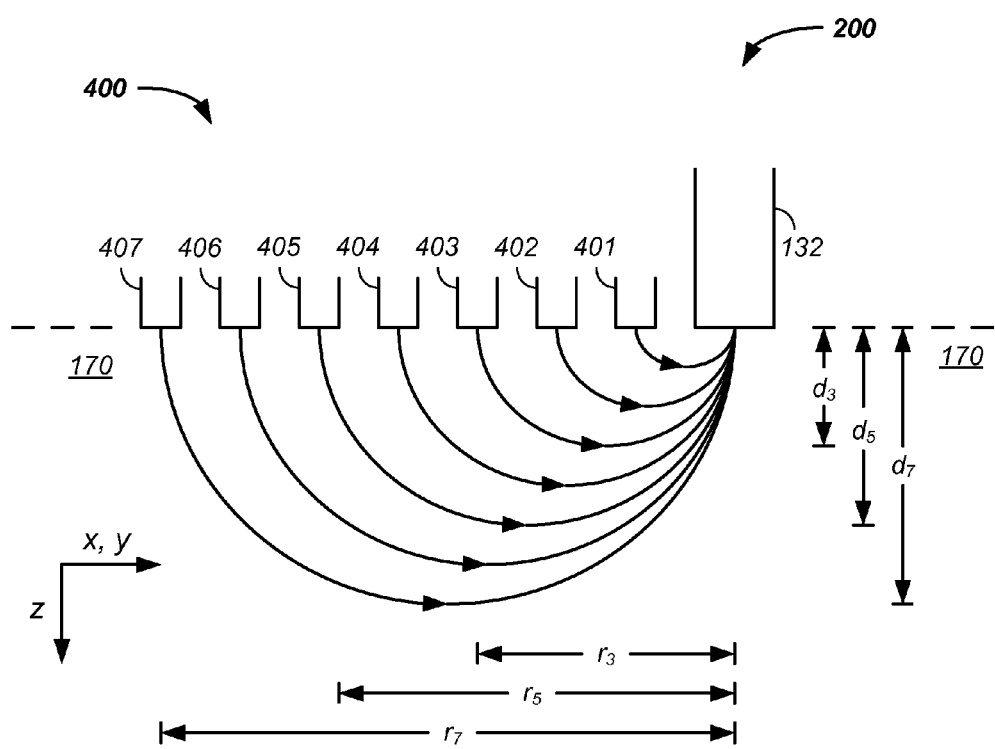
FIG. 4 illustrates varying illumination zones relative to a detector.

In the first case of the spatial resolution method, referring now to FIG. 4, the photon transit system 200 uses a vector or array of illumination sources 400, of the source system 110, in a spatially resolved pathlength determination system. For example, the illumination sources are an array of fiber optic cables. In this example, a set of seven fiber optics 401, 402, 403, 404, 405, 406, 407 are positioned, radially along the x,y plane of the subject 170 to provide a set of illuminations zones, relative to a detection fiber at a detection zone. As illustrated the third illumination fiber optic 403/detector 132 combination yields a mean photon path having a third depth of penetration, $d_3$, for a third fiber optic-to-detector radial distance, $r_3$; the fifth illumination fiber optic 405/detector 132 combination yields a mean photon path having a fifth depth of penetration, $d_5$, for a fifth fiber optic-to-detector radial distance, $r_5$; and the seventh illumination fiber optic 407/detector 132 combination yields a mean photon path having a seventh depth of penetration, $d_7$, for a seventh fiber optic-to-detector radial distance, $r_7$. Generally, for photons in the near-infrared region from 1100 to 2500 nanometers both a mean depth of penetration of the photons and a total optical pathlength increases with increasing fiber optic-to-detector distance, where the fiber optic-to-detector distance is less than about three millimeters.

Figure 5:
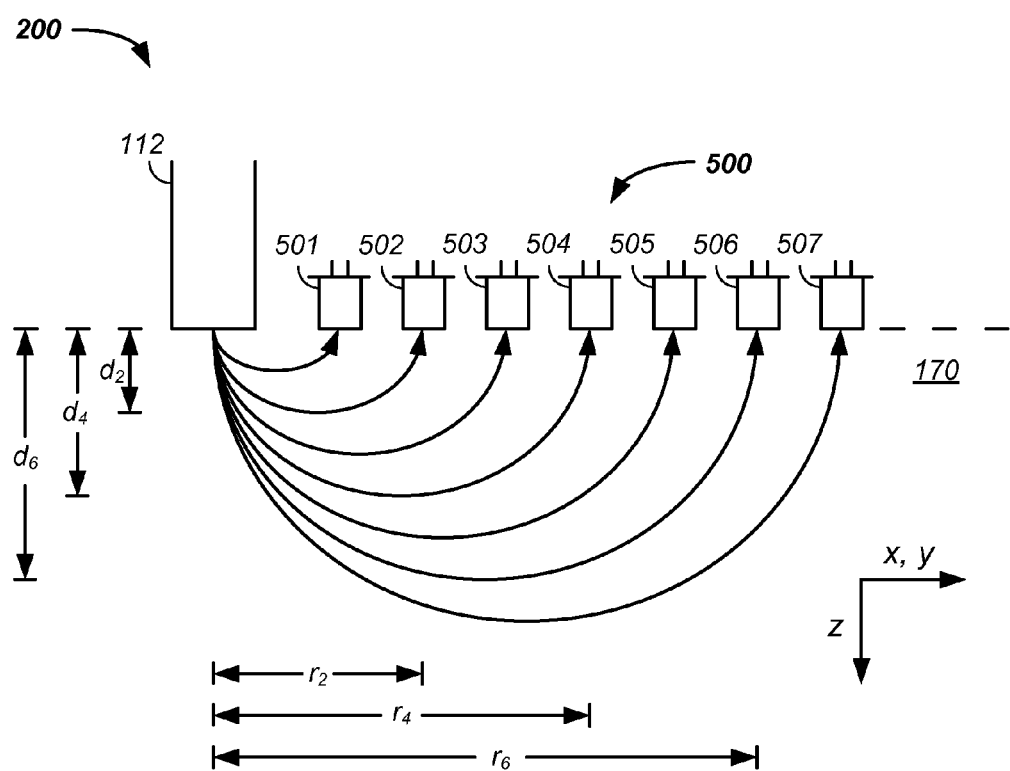
FIG. 5 illustrates varying detection zones relative to an illuminator.

In the second case of the spatial resolution method, referring now to FIG. 5, the photon transit system 200 uses a vector or array of detectors 500 in the detection system 130. For example, a single fiber optic source is used, which sends radially distributed light to an array of staring detectors or collection optics coupled to a set of detectors. In this example, a set of seven detectors 501, 502, 503, 504, 505, 506, 507 are positioned, radially along the x,y plane to provide a set of detection zones, relative to an illumination zone. As illustrated the source 112/second detector 502 combination yields a mean photon path having a second depth of penetration, $d_2$, for a second source-to-detector radial distance, $r_2$; the source 112/fourth detector 504 combination yields a mean photon path having a fourth depth of penetration, $d_4$, for a fourth source-to-detector radial distance, $r_4$; and the source 112/sixth detector 506 combination yields a mean photon path having a sixth depth of penetration, $d_6$, for a sixth source-to-detector radial distance, $r_6$. Again, generally for photons in the near-infrared region from 1100 to 2500 nanometers both the mean depth of penetration of the photons into skin and the total optical pathlength in skin increases with increasing fiber optic-to-detector distance, where the fiber optic-to-detector distance is less than about three millimeters. Hence, data collected with an analyzer configured with a multiple detector design generally corresponds to the first case of a multiple source design.

Referring again to FIGS. 4 and 5, the number of source zones, where light enters skin of the subject 170, from one or more source elements, is optionally 1, 2, 3, 4, 5, 10, 20, 50, 100 or more and the number of detection zones, where light exiting the skin of the subject 170 is detected by one or more detection elements and/or systems, is optionally 1, 2, 3, 4, 5, 10, 20, 50, 100, 500, 1000, 5000, 10,000, 50,000 or more.

Temporal Resolution

The second method of temporal resolution is optionally performed in a number of manners. For clarity of presentation and without limitation, a temporal resolution example is provided where photons are timed using a gating system and the elapsed time is used to determine photon paths in tissue.

Referring now to FIGS. 6A-D, an example of a temporally resolved gating system 600 is illustrated. Generally, in the temporal gating system 600 the time of flight of a photon is used to determine the pathlength, b. Referring now to FIG. 6A, at an initial time, $t_0$, an interrogation pulse 610 of one or more photons is introduced to the sample, which herein is skin of the subject 170. The interrogation pulse 610 is also referred to as a pump pulse or as a flash of light. At one or more subsequent gated detection times 620, after passing through the sample the interrogation pulse 610 is detected. As illustrated, the gated detection times are at a first time 622, $t_1$; a second time 624, $t_2$; a third time 626, $t_3$; and at an $n^{th}$ time 628, $t_n$, where n is a positive number. Optionally, the gated detection times 620 overlap. For the near-infrared spectral region, the elapsed time used to detect the interrogation photons 610 is on the order of picoseconds, such as less than about 100, 10, or 1 picosecond. The physical pathlength, b, is determined using equation 2:

$$OPD = \frac{c}{n}(b) \qquad (\text{eq. 2})$$

where OPD is the optical path distance, c is the speed of light, n is the index of refraction of the sample, an index of refraction of a portion of the sample or an average index of refraction of the sample, and b is the physical pathlength. Optionally, n is a mathematical representation of a series of indices of refraction of various constituents of skin and/or skin and surrounding tissue layers. More generally, observed pathlength is related to elapsed time between photon launch and photon detection where the pathlength of photons in the sample is related to elapsed time, optionally with one or more additional variables related to one or more refractive indices.

Referring now to FIG. 6B, illustrative paths of the photons for the first gated detection time 622 are provided. A first path, $p_{1a}$; second path, $p_{1b}$; and third path, $p_{1c}$, of photons in the tissue are illustrated. In each case, the total pathlength, for a constant index of refraction, is the same for each path. However, the probability of each path also depends on the anisotropy of the tissue and the variable indices of refraction of traversed tissue voxels.

Referring now to FIG. 6C, illustrative paths of the photons for the second gated detection time 624 are provided. A first path, $p_{2a}$; second path, $p_{2b}$; and third path, $p_{2c}$, of photons in the tissue are illustrated. Again, in each case the total pathlength for the second elapsed time, $t_2$, is the same for each path. Generally, if the delay to the second gated detection time 624 is twice as long as the first gated detection time 622, then the second pathlength, $p_2$, for the second gated detection time 624 is twice as long as the first pathlength, $p_1$, for the first gated detection time 622. Knowledge of anisotropy is optionally used to decrease the probability spread of paths observed in the second set of pathlengths, $p_{2a}$, $p_{2a}$, $p_{2b}$, $p_{2c}$. Similarly a-priori knowledge of approximate physiological thickness of varying tissue layers, such as an epidermal thickness of a patient, an average epidermal thickness of a population, a dermal thickness of a patient, and/or an average dermal thickness of a population is optionally used to reduce error in an estimation of pathlength, a product of pathlength and a molar absorptivity, and/or a glucose concentration by limiting bounds of probability of a photon traversing different pathways through the skin layers and still returning to the detection element with the elapsed time. Similarly, knowledge of an index of refraction of one or more sample constituents and/or a mathematical representation of probable indices of refraction is also optionally used to reduce error in estimation of a pathlength, molar absorptivity, and/or an analyte property concentration estimation. Still further, knowledge of an incident point or region of light entering she skin of the subject relative to a detection zone is optionally used to further determine probability of a photon traversing dermal or subcutaneous fat layers along with bounding errors of pathlength in each layer.

Referring now to FIG. 6D, mean pathlengths and trajectories are illustrated for three elapsed times, $t_1$, $t_2$, $t_3$. As with the spatially resolved method, generally, for photons in the near-infrared region from 1100 to 2500 nanometers, both a mean depth of penetration of the photons, $d_n$; the total radial distance traveled, $r_m$; and the total optical pathlength increases with increasing time, where the fiber optic-to-detector distance is less than about three millimeters. Elapsed time are preferably faster than 100 nanoseconds and slower than 100 picoseconds, such as about 1, 5, 10, and 50 picoseconds.

Spatial and Temporal Resolution

Hence, both the spatial resolution method and temporal resolution method yield information on pathlength, b, which is optionally used by the data processing system 140 to reduce error in the determined concentration, C.

Analyzer and Subject Variation

As described, supra, Beer's Law states that absorbance, A, is proportional to pathlength, b, times concentration, C. More precisely, Beer's Law includes a molar absorbance, $\epsilon$, term, as shown in equation 3:

$$A=\epsilon bC \qquad (eq.\ 3)$$

Typically, spectroscopists consider the molar absorbance as a constant due to the difficulties in determination of the molar absorbance for a complex sample, such as skin of the subject 170. However, information related to the combined molar absorbance and pathlength product for skin tissue of individuals is optionally determined using one or both of the spatially resolved method and time resolved method, described supra. In the field of noninvasive glucose concentration determination, the product of molar absorbance and pathlength relates at least to the dermal thickness of the particular individual or subject 170 being analyzed. Examples of spatially resolved analyzer methods used to provide information on the molar absorbance and/or pathlength usable in reduction of analyte property estimation or determination are provided infra.

Spatially Resolved Analyzer

Herein, an analyzer 100 using fiber optics is used to describe obtaining spatially resolved information, such as pathlength and/or molar absorbance, of skin of an individual, which is subsequently used by the data processing system 140. The use of fiber optics in the examples is used without limitation, without loss of generality, and for clarity of presentation. More generally, photons are delivered in quantities of one or more through free space, through optics, and/or off of reflectors to the skin of the subject 170 as a function of distance from a detection zone.

Figure 7A:
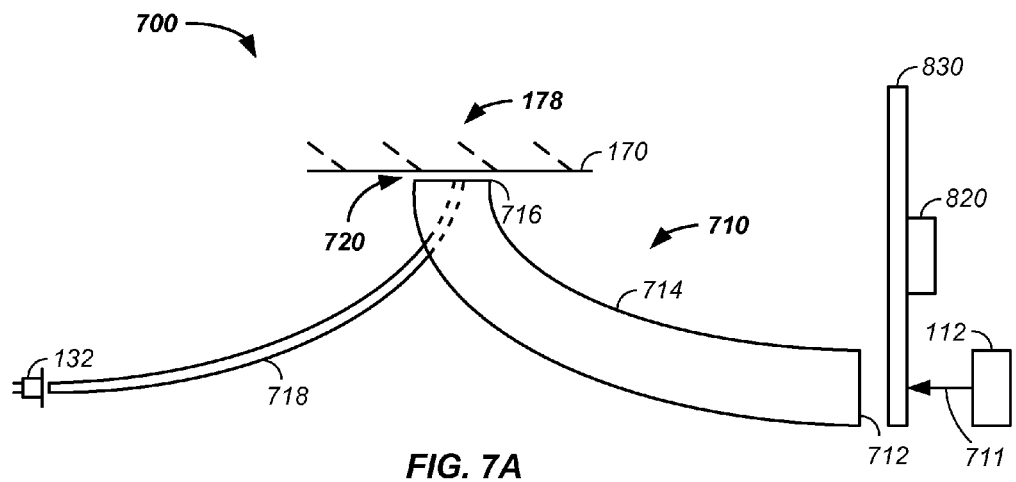
FIGS. 7(A-C) illustrate a fiber optic bundle, FIG. 7A; a first example sample interface end of the fiber optic bundle, FIG. 7B; and a second example sample interface end of the fiber optic bundle, FIG. 7C.

Referring now to FIG. 7A, an example of a fiber optic interface system 700 of the analyzer 100 to the subject 170 is provided, which is an example of the sample interface system 150. Light from the source system 110 of the analyzer 100 is coupled into a fiber optic illumination bundle 714 of a fiber optic bundle 710. The fiber optic illumination bundle 714 guides light to a sample site 178 of the subject 170. The sample site 178 has a surface area and a sample volume. In a first case, a sample interface tip 716 of the fiber optic bundle 710 contacts the subject 170 at the sample site 178. In a second case, the sample interface tip 716 of the fiber optic bundle 710 proximately contacts the subject 170 at the sample site 178, but leaves a gap 720 between the sample interface tip 716 of the fiber optic bundle 710 and the subject 170. In one instance, the gap 720 is filled with a contact fluid and/or an optical contact fluid. In a second instance, the gap 720 is filled with air, such as atmospheric air. Light transported by the fiber optic bundle 710 to the subject 170 interacts with tissue of the subject 170 at the sample site 178. A portion of the light interacting with the sample site is collected with one or more fiber optic collection fibers 718, which is optionally and preferably integrated into the fiber optic bundle 710. As illustrated, a single collection fiber 718 is used. The collection fiber 718 transports collected light to the detector 132 of the detection system 130.

Figure 7B:
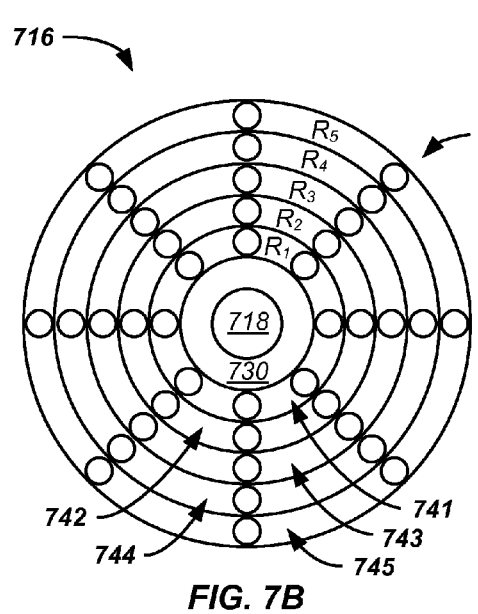

Referring now to FIG. 7B, a first example of a sample side light collection end 716 of the fiber optic bundle 710 is illustrated. In this example, the single collection fiber 718 is circumferentially surrounded by an optional spacer 730, where the spacer has an average radial width of less than about 200, 150, 100, 50, or 25 micrometers. The optional spacer 730 is circumferentially surrounded by a set of fiber optic elements 713. As illustrated, the set of fiber optic elements 713 are arranged into a set of radial dispersed fiber optic rings, such as a first ring 741, a second ring 742, a third ring 743, a fourth ring 744, and an $n^{th}$ ring 745, where n comprises a positive integer of at least 2, 3, 4, 5, 6, 7, 8, 9, or 10. Optionally, the fiber optic elements 713 are in any configuration, such as in a close-packed configuration about the collection fiber 718 or in an about close-packed configuration about the collection fiber 718. The distance of each individual fiber optic of the set of fiber optic elements 713, or light collection element, from the center of the collection fiber 718 is preferably known.

Figure 7C:
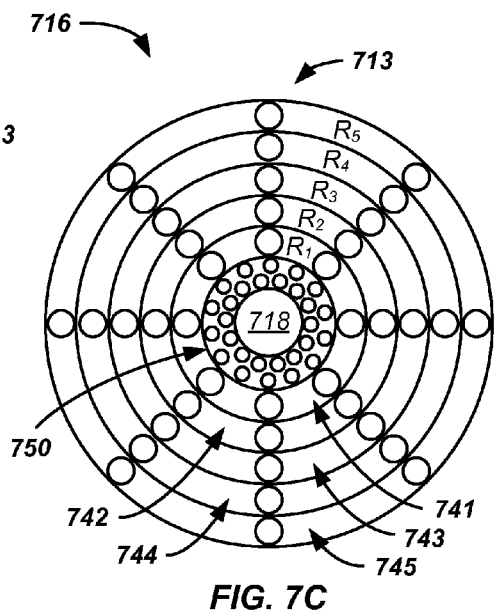

Referring now to FIG. 7C, a second example of the sample side light collection end 716 of the fiber optic bundle 710 is provided. In this example, the centrally positioned collection fiber 718 is circumferentially surrounded by a set of spacer fibers 750. The spacer fibers combine to cover a radial distance from the outside of the collection fiber of less than about 300, 200, 150, 100, 75, 60, 50, or 40 micrometers. The spacer fibers 750 are circumferentially surrounded by the radially dispersed fiber optic rings, such as the first ring 741, the second ring 742, the third ring 743, the fourth ring 744, and the $n^{th}$ ring 745. Optionally, fiber diameters of the spacer fibers 750 are at least ten, twenty, or thirty percent larger or smaller than fiber diameters of the set of fiber optic elements 713. Further, optionally the fiber optic elements 713 are arranged in any spatial configuration radially outward from the spacer fibers 750. More generally, the set of fiber optic elements 713 and/or spacer fibers 750 optionally contain two, three, four, or more fiber optic diameters, such as any of about 40, 50, 60, 80, 100, 150, 200, or more micrometers. Optionally, smaller diameter fiber optics, or light collection optics, are positioned closer to any detection fiber and progressively larger diameter fiber optics are positioned, relative to the smaller diameter fiber optics, further from the detection fiber.

Radial Distribution System

Referring now to FIG. 8A, FIG. 8B and FIG. 9, and FIGS. 10 A-D a system for spatial illumination 800 of the sample site 178 of the subject 170 is provided. The spatial illumination system 800 is used to control distances between illumination zones and detection zones as a function of time. In a first case, light is distributed radially relative to a detection zone using a fiber optic bundle. In a second case, light is distributed radially relative to a detection zone using a reflective optic system and/or a lens system. Generally, the first case and second case are non-limiting examples of radial distribution of light about one or more detection zones as a function of time.

Radial Position Using Fiber Optics

Referring now to FIG. 8A, a third example of the sample side light collection end 716 of the fiber optic bundle 710 is provided. In this example, the collection fiber 718 or collection optic is circumferentially surrounded by the set of fiber optic elements 713 or irradiation points on the skin of the subject 170. For clarity of presentation and without loss of generality, the fiber optic elements 713 are depicted in a set of rings radially distributed from the collection fiber 718. However, it is understood that the set of fiber optics 713 are optionally close packed, arranged in a random configuration, or arranged according to any criterion. Notably, the distance of each fiber optic element of the set of fiber optic elements 713 from the collection fiber 718 is optionally determined using standard measurement techniques through use of an algorithm and/or through use of a dynamically adjustable optic used to deliver light to the sample, such as through air. Hence, the radial distribution approach, described infra, is optionally used for individual fiber optic elements and/or groups of fiber optic elements arranged in any configuration. More generally, the radial distribution approach, described infra, is optionally used for any set of illumination zone/ detection zone distances using any form of illuminator and any form of detection system, such as through use of the spatially resolved system and/or the time resolved system.

Referring now to FIG. 8B, an example of a light input end 712 of the fiber optic bundle 710 is provided. In this example, individual fibers of the set of fiber optics 713 having the same or closely spaced radial distances from the collection fiber 718 are grouped into a set of fiber optic bundles or a set of fiber optic bundlets 810. As illustrated, the seven fibers in the first ring circumferentially surrounding the collection fiber 718 are grouped into a first bundlet 811. Similarly, the sixteen fibers in the second ring circumferentially surrounding the collection fiber 718 are grouped into a second bundlet 812. Similarly, the fibers from the third, fourth, fifth, and sixth rings about the collection fiber 718 at the sample side illumination end 716 of the fiber bundle 710 are grouped into a third bundlet 813, a fourth bundlet 814, a fifth bundlet 815, and a sixth bundlet 816, respectively. For clarity of presentation, the individual fibers are not illustrated in the second, third, fourth, fifth, and sixth bundlets 812, 813, 814, 815, 816. Individual bundles and/or individual fibers of the set of fiber optic bundlets 810 are optionally selectively illuminated using a mask 820, described infra.

Referring now to FIG. 9 and FIG. 7A, a mask wheel 830 is illustrated. Generally, the mask wheel 830 rotates, such as through use of a wheel motor 820. As a function of mask wheel rotation position, holes or apertures through the mask wheel 830 selectively pass light from the source system 110 to the fiber optic input end 712 of the fiber optic bundle 710. In practice, the apertures through the mask wheel are precisely located to align with (1) individual fiber optic elements of the set of fiber optics at the input end 712 of the fiber optic bundle or (2) individual bundlets of the set of fiber optic bundlets 810. Optionally an encoder or marker section 840 of the mask wheel 830 is used for tracking, determining, and/or validating wheel position in use.

Still referring to FIG. 9, an example of use of the mask wheel 830 to selectively illuminate individual bundlets of the set of fiber optic bundlets 810 is provided. Herein, for clarity of presentation the individual bundlets are each presented as uniform size, are exaggerated in size, and are repositioned on the wheel. For example, as illustrated a first mask position, $p_1$, 821 is illustrated at about the seven o'clock position. The first mask position 821 figuratively illustrates an aperture passing light from the source system 110 to the first bundlet 811 while blocking light to the second through sixth bundlets 812-816. At a second point in time, the mask wheel 830 is rotated such that a second mask position, $p_2$, 822 is aligned with the input end 712 of the fiber optic bundle 710. As illustrated, at the second point in time, the mask wheel 830 passes light from the illumination system 110 to the second bundlet 812, while blocking light to the first bundlet 811 and blocking light to the third through six bundlets 813-816. Similarly, at a third point in time the mask wheel uses a third mask position, $p_3$, 823 to selectively pass light into only the fifth bundlet 815. Similarly, at a fourth point in time the mask wheel uses a fourth mask position, $p_4$, 824 to selectively pass light into only the sixth bundlet 816.

Still referring to FIG. 9, thus far the immediately prior example has only shown individual illuminated bundlets as a function of time. However, combinations of bundlets are optionally illuminated as a function of time. In this continuing example, at a fifth point in time, the mask wheel 830 is rotated such that a fifth mask position, $p_5$, 825 is aligned with the input end 712 of the fiber optic bundle 710. As illustrated, at the fifth point in time, the mask wheel 830 passes light from the illumination system 110 to all of (1) the second bundlet 812, (2) the third bundlet 813, and (3) the fourth bundlet 814, while blocking light to all of (1) the first bundlet 811, (2) the fifth bundlet 815, and (3) the sixth bundlet 816. Similarly, at a sixth point in time a sixth mask position, $p_6$, 826 of the mask wheel 830 passes light to the second through fifth bundlets 812-815 while blocking light to both the first bundlet 811 and sixth bundlet 816.

In practice, the mask wheel 830 contains an integral number of n positions, where the n positions selectively illuminate and/or block any combination of: (1) the individual fibers of the set of fiber optics 713 and/or (2) bundlets 810 of the set of fiber optic optics 713. Further, the filter wheel is optionally of any shape and uses any number of motors to position mask position openings relative to selected fiber optics. Still further, in practice the filter wheel is optionally any electro-mechanical and/or electro-optical system used to selectively illuminate the individual fibers of the set of fiber optics 713. Yet still further, in practice the filter wheel is optionally any illumination system that selectively passes light to any illumination optic or illumination zone, where various illumination zones illuminate various regions of the subject 170 as a function of time. The various illumination zones alter the effectively probed sample site 178 or region of the subject 170.

Radial Position Using a Mirror and/or Lens System

Referring now to FIG. 10, a dynamically positioned optic system 1000 for directing incident light to a radially changing position about a collection zone is provided.

Figure 10A:
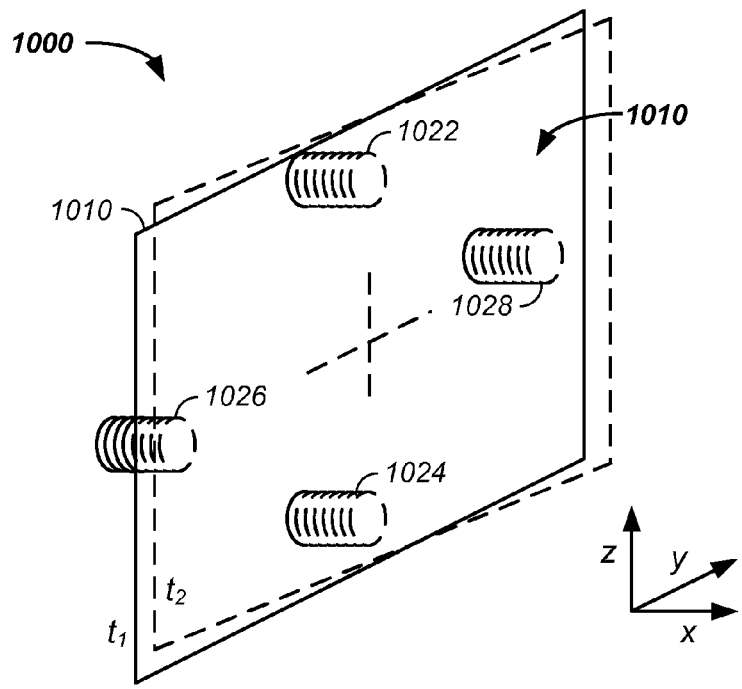
FIG. 10A illustrates a position selection optic.

Referring now to FIG. 10A, a mirror 1010 is illustrative of any mirror, lens, mirror system, and/or lens system used to dynamically and positionally direct incident light to one or more illumination zones of the subject 170 relative to one or more detection zones and/or volumes monitored by the photon transport system 120 and/or the detector system 130.

Still more generally, the data processing system 140 and/or the system controller 180 optionally control one or more optics, figuratively illustrated as the mirror 1010, to dynamically control incident light 711 on the subject 170 relative to a detection zone on the subject 170 that combine to form the sample site 178 through control of one or more of:

x-axis position of the incident light 711 on the subject 170;
y-axis position of the incident light 711 on the subject 170;
solid angle of the incident light 711 on a single fiber of the fiber bundle 710;
solid angle of incident light 711 on a set of fibers of the fiber bundle 710;
a cross-sectional diameter or width of the incident light 711;
an incident angle of the incident light 711 on the subject 170 relative to an axis perpendicular to skin of the subject 170 where the incident light 711 interfaces to the subject 170;
focusing of the incident light 711; and/or
depth of focus of the incident light 711 on the subject 170.

Several examples are provided, infra, to further illustrate the use of the system controller 180 to control shape, position, and/or angle of the incident light 711 reaching a fiber optic bundle, skin of the subject 170, and/or an element of the photon transport system 120.

Referring again to FIG. 10A, an example is provided of light directed by the photon transport system 120 from the source system 110 to the subject directly, through one or more fiber optic of the fiber optic bundle 710, and/or through the photon transport system 120. However, orientation of the mirror 1010 is varied as a function of time relative to an incident set of photons pathway. For example, the mirror 1010 is translated along the x-axis of the mean optical path, is rotated about the y-axis of the mean optical path, and/or is rotated about the z-axis of the mean optical path of the analyzer 100. For example, a first mirror movement element 1022, such as a first spring, and a second mirror movement element 1024, such as a second spring, combine to rotate the mirror about the y-axis as illustrated. Similarly, a third mirror movement element 1026, such as a third spring, and a fourth mirror movement element 1028, such as a fourth spring, combine to rotate the mirror about the z-axis as illustrated in the second time position, $t_2$, relative to a first time position, $t_1$.

Figure 10B:
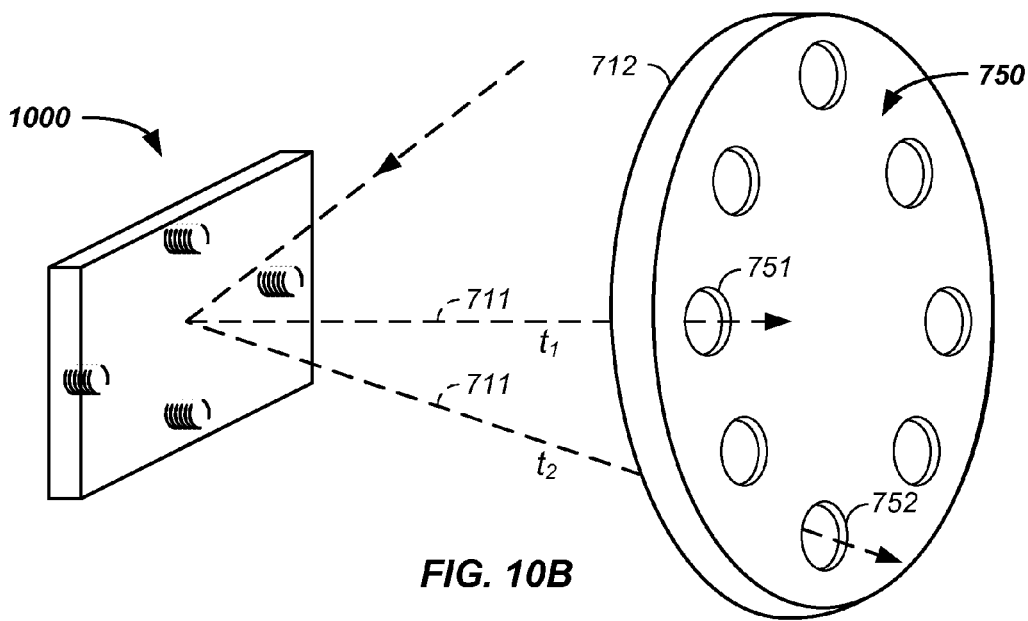
FIG. 10B illustrates the position selection optic selecting position.
Figure 10C:
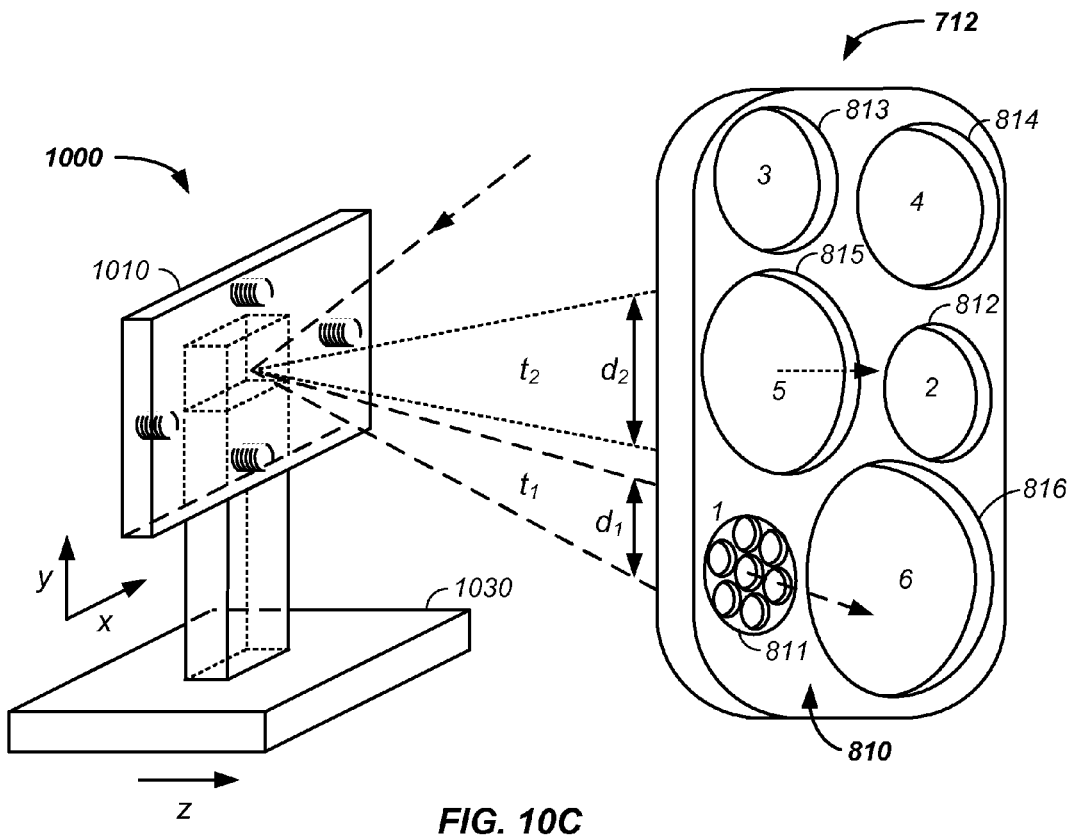
FIG. 10C illustrates solid angle selection using the position selection optic.

Referring now to FIG. 10B, an example of the dynamically positioned optic system 1000 directing the incident light 711 to a plurality of positions as a function of time is provided. As illustrated, the mirror 1010 directs light to the light input end 712 of the fiber bundle 710. Particularly, the incident light 711 is directed at a first time, $t_1$, to a first fiber optic 751 and the incident light 711 is directed at a second time, $t_2$, to a second fiber optic 752 of a set of fiber optics 750. However, more generally, the dynamically positioned optic system 1000 directs the incident light using the mirror 1000 to any y-, z-axis position along the x-axis of the incident light as a function of time, such as to any optic and/or to a controlled position of skin of the subject 170.

In one non-limiting example, a computer controlled tiltable optic is configured to: (1) optionally irradiate the subject with photons at a first mean angle off of a first axis perpendicular to the subject at the first distance of a set of mean radial distances; (2) subsequently and optionally irradiate the subject with the photons at a second mean angle off of a second axis perpendicular to the subject at the second distance of the set of mean radial distances, where the first mean angle and the second mean angle differ by at least ten degrees; and to optionally direct photons at a third mean angle off of a third axis perpendicular to the subject at the third distance of the set of mean radial distances, where the first mean angle and the third mean angle differ by at least ten degrees and/or where the second mean angle and the third mean angle differ by at least five degrees Referring now to FIG. 10C, an example of the dynamically positioned optic system 1000 directing the incident light to a plurality of positions with a controllable and varying as a function of time solid angle is provided. Optionally, the solid angle is fixed as a function of time and the position of the incident light 711 onto the light input end 712 of the fiber bundle 710 is varied, under control of the system controller 180 as a function of time. As illustrated, the mirror 1010 directs light to the light input end 712 of the fiber bundle 710 where the fiber bundle 710 includes one or more bundlets, such as the set of fiber optic bundlets 810. In this example, the incident light is directed at a first time, $t_1$, with a first solid angle to a first fiber optic bunch or group, such as the first bundlet 811, described supra, and at a second time, $t_2$, with a second solid angle to a second fiber optic bunch, such as the second bundlet 812, described supra. However, more generally, the dynamically positioned optic system 1000 directs the incident light to any y-, z-axis position along the x-axis of the incident light as a function of time at any solid angle or with any focusing angle, such as to any optic, any group of optics, and/or to a controlled position and/or size of skin of the subject 170 relative to a detection zone.

Figure 10D:
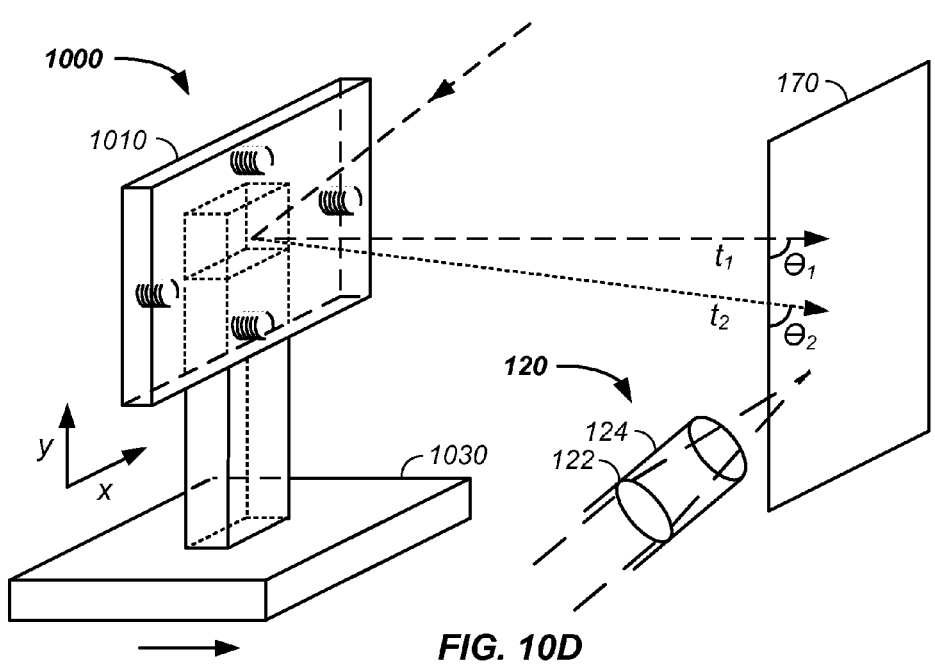
FIG. 10D illustrates radial control of incident light relative to a detection zone.

Referring now to FIG. 10D, an example is provided of the dynamically positioned optic system 1000 directing the incident light to a plurality of positions with a varying incident angle onto skin of the subject 170. As illustrated, the mirror 1010 directs light directly to the subject 170 without an optic touching the subject 170 or without touching a coupling fluid on the subject 170. However, alternatively the light is redirected after the mirror 1010, such as with a grins lens on a fiber optic element of the fiber optic bundle 710. In this example, the incident light is directed at a first time, $t_1$, with a first incident angle, $\Theta_1$, and at a second time, $t_2$, with a second incident angle, $\Theta_2$. However, more generally, the dynamically positioned optic system 1000 directs the incident light to any y-, z-axis position along the x-axis of the incident light as a function of time at any solid angle, with any focusing depth, and/or an any incident angle, such as to any optic and/or to a controlled position and/or size of skin of the subject 170 relative to a detection zone. In this example, the detection zone is a volume of the subject monitored by the photon transport system 120 and/or an lens or mirror of the photon transport system 120 as interacting with the detector system 130 and a detector therein.

Adaptive Subject Measurement

Delivery of the incident light 711 to the subject 170 is optionally varied in time in terms of position, radial position relative to a point of the skin of the subject 170, solid angle, incident angle, depth of focus, energy, and/or intensity. Herein, without limitation a spatial illumination system is used to illustrate the controlled and variable use of incident light.

Figure 11A:
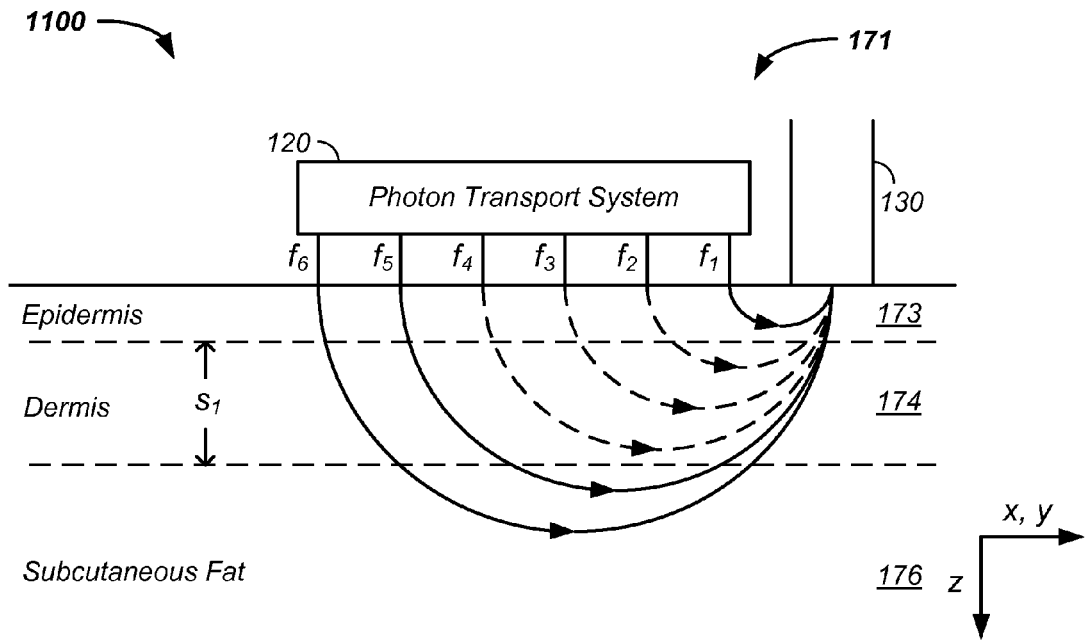
FIGS. 11(A-B) illustrate a pathlength resolved sample interface for (1) a first subject, FIG. 11A and (2) a second subject, FIG. 11B.
Figure 11B:
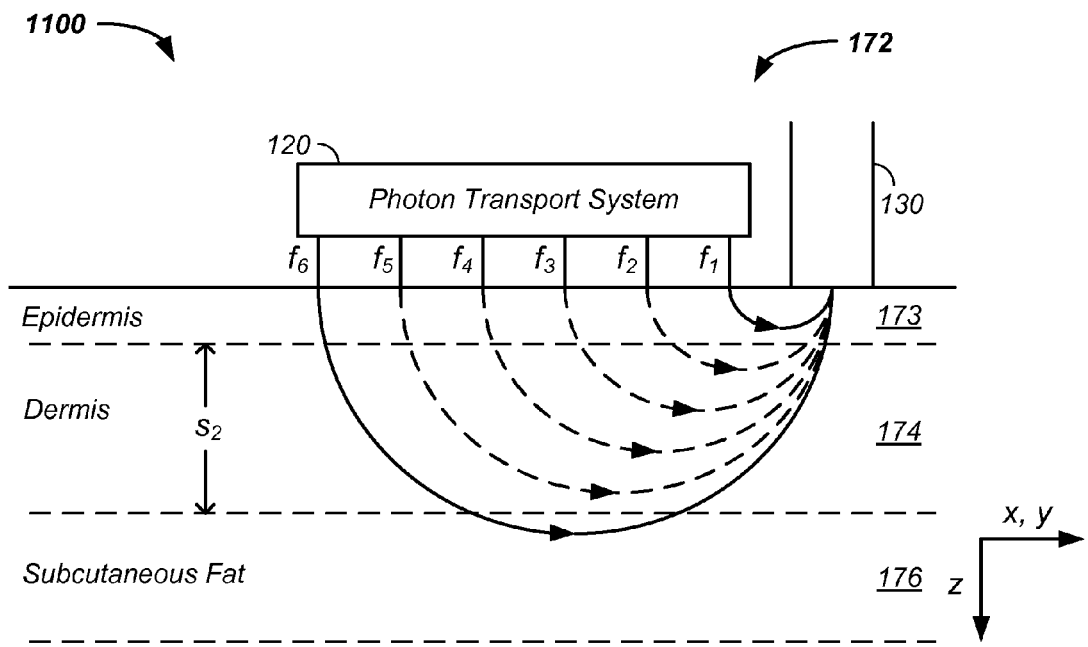

Referring now to FIG. 11A and FIG. 11B, examples of use of a spatial illumination system 1100 are illustrated for a first subject 171 and a second subject 172. However, while the examples provided in this section use a fiber optic bundle to illustrate radially controlled irradiation of the sample, the examples are also illustrative of use of the dynamically positioned optic system 1000 for directing incident light to a radially changing position about a collection zone. Still more generally the photon transport system 120 in FIGS. 11A and 11B is used in any spatially resolved system and/or in any time resolved system to deliver photons as a function of radial distance to a detector or to a detection zone.

Referring now to FIG. 11A and FIG. 9, an example of application of the spatial illumination system 800 to the first subject 171 is provided. At a first point in time, the first position, $p_1$, 821 of the filter wheel 830 is aligned with the light input end 712 of the fiber bundle 710, which results in the light from the first bundlet 811, which corresponds to the first ring 741, irradiating the sample site 178 at a first radial distance, $r_1$, and a first depth, $d_1$, which as illustrated in FIG. 11A has a mean optical path through the epidermis. Similarly, at a second point in time, the filter wheel 830 at the second position 822 passes light to the second bundlet 812, which corresponds to the second ring, irradiating the sample site 178 at a second increased distance and a second increased depth, which as illustrated in FIG. 11A has a mean optical path through the epidermis and dermis. The dynamically positioned optic system 1000 is optionally used to direct light as a function of time to the first position 821 and subsequently to the second position 822. Similarly, results of interrogation of the subject 170 with light passed through the six illustrative fiber illumination rings in FIG. 8A is provided in Table 1. The results of Table 1 demonstrate that for the first individual, the prime illumination rings for a blood analyte concentration determination are rings two through four as the first ring, sampling the epidermis, does not sample the blood filled dermis layer; rings two through four probe the blood filled dermis layer; and rings five and six penetrate through the dermis into the subcutaneous fat where photons are lost and the resultant signal-to-noise ratio for the blood analyte decreases.

TABLE 1

| Subject 1 | |
|---|---|
| Illumination Ring | Deepest Tissue Layer Probed |
| 1 | Epidermis |
| 2 | Dermis |
| 3 | Dermis |
| 4 | Dermis |
| 5 | Subcutaneous Fat |
| 6 | Subcutaneous Fat |

Referring now to FIG. 11B and FIG. 8A, an example of application of the spatial illumination system 800 to the second subject 172 is provided. Again, the dynamically positioned optic system 1000 is optionally used to deliver light to the spatial illumination system 800. Results of interrogation of the subject 170 with light passed through the six illustrative fiber illumination rings in FIG. 8A is provided in Table 2. For the second subject, it is noted that interrogation of the sample with the fifth radial fiber ring, $f_5$, results in a mean optical path through the epidermis and dermis, but not through the subcutaneous fat. In stark contrast, the mean optical path using the fifth radial fiber ring, $f_5$, for the second subject 172 has a deepest penetration depth into the dermis 174. Hence, the fifth radial fiber ring, $f_5$, yields photons probing the subcutaneous fat 176 for the first subject 171 and yields photons probing the dermis 174 of the second subject 172. Hence, for a water soluble analyte and/or a blood borne analyte, such as glucose, the analyzer 100 is more optimally configured to not use both the fifth fiber ring, $f_5$, and the sixth fiber ring, $f_6$, for the first subject 171. However, analyzer 100 is more optimally configured to not use only the sixth fiber ring, $f_6$, for the second subject 172, as described infra.

TABLE 2

| Subject 2 | |
|---|---|
| Illumination Ring | Deepest Tissue Layer Probed |
| 1 | Epidermis |
| 2 | Dermis |
| 3 | Dermis |
| 4 | Dermis |
| 5 | Dermis |
| 6 | Subcutaneous Fat |

In yet another example, light is delivered with known radial distance to the detection zone, such as with optics of the analyzer, without use of a fiber optic bundle and/or without the use of a filter wheel. Just as the illumination ring determines the deepest tissue layer probed, control of the irradiation zone/detection zone distance determines the deepest tissue layer probed.

Incident Light Control

Referring again to FIGS. 10A-D, the dynamically positioned optic system 1000 is optionally used as a function of time to control one or more of:

delivery of the incident light 711 to a single selected fiber optic of the fiber optic bundle 710;

delivery of the incident light 711 to a selected bundlet of the set of fiber optic bundlets 810, such as to the first bundlet 811 at a first point in time and to the second bundlet 812 at a second point in time;

variation of solid angle of the incident light 711 to an optic and/or to the subject 170;

variation of radial position of delivery of the incident light 711 relative to a fixed location, such as a center of an optic, a target point on skin of the subject 170, or a center of the sample site 178;

incident angle of the incident light 711 relative to a plane tangential to the skin of the subject 170 and/or an axis normal to the skin of the subject 170 at the sample site 178;

apparent focus depth of the incident light 711 into the skin of the subject 170;

energy; and intensity, such as number of photon per second varying from one point in time to another by greater than 1, 10, 50, 100, 500, 1000, or 5000 percent.

Time Resolved Spectroscopy

In still yet another example, referring again to time resolved spectroscopy, instead of delivering light through the filter wheel to force radial distance, photons are optionally delivered to the skin and the time resolved gating system is used to determine probably photon penetration depth. For example, Table 3 shows that at greater elapsed time to the $n^{th}$ gated detection period, the probability of the deepest penetration depth reaching deeper tissue layers increases.

TABLE 3

Time Resolved Spectroscopy

| Elapsed Time (picoseconds) | Deepest Tissue Layer Probed |
| --- | --- |
| 1 | Epidermis |
| 10 | Dermis |
| 50 | Dermis |
| 100 | Subcutaneous Fat |

Data Processing

Figure 12:
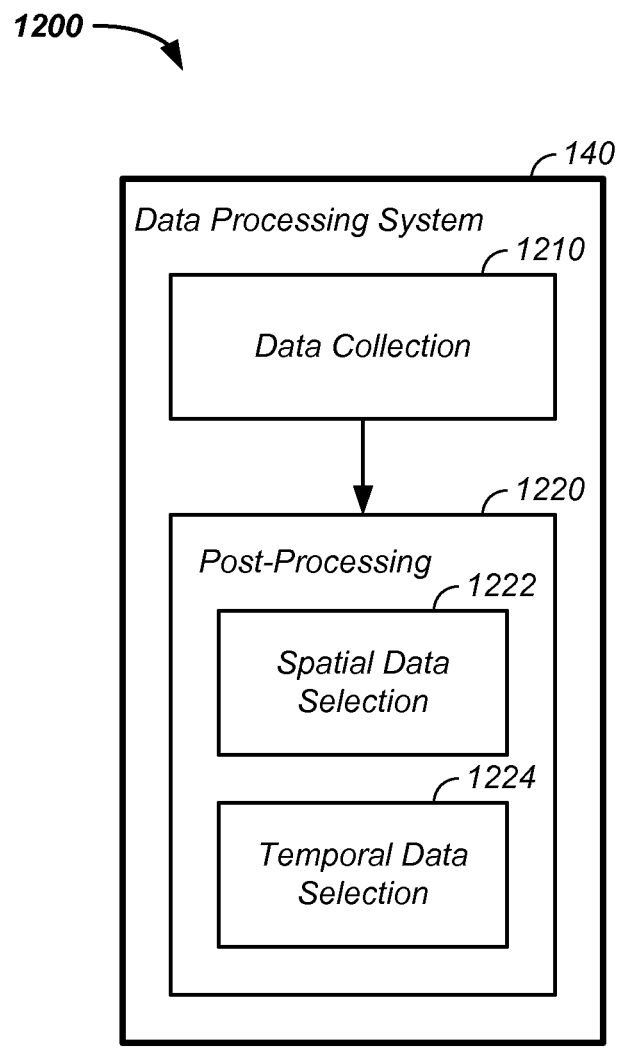
FIG. 12 provides a method of use of a data processing system.

Referring now to FIG. 12, the data processing system 140 is further described. The data processing system 140 is optionally uses a step of post-processing 1120 to process a set of collected data 1210. The post-processing step 1120 optionally operates on data collected as a function of any of: radial distance of the incident light 711 to a reference point, such as a detector; solid angle of the incident light 711 relative to the subject 170; angle of the incident light 711 relative to skin of the subject 170; and/or depth of focus of the incident light 711 relative to a surface of the skin of the subject 170.

Two-Phase Measurement(s)

Referring again to FIG. 11A and FIG. 11B, a first optional two-phase measurement approach is herein described. Optionally, during a first sample mapping phase, the photon transport system 120 provides interrogation photons to a particular test subject at controlled, but varying, radial distances from the detection system 130. One or more spectral markers, or an algorithmic/mathematical representation thereof, are used to determine the radial illumination distances best used for the particular test subject. An output of the first phase is the data processing system 140 selecting how to illuminate/irradiate the subject 170. Subsequently, during a second data collection phase, the system controller 180 controls the photon transport system 120 to deliver photons over selected conditions to the subject 170. For clarity, several illustrative examples are provided, infra.

In a first example, a first spectral marker is optionally related to the absorbance of the subcutaneous fat 176 for the first subject 171. During the first sample mapping phase, the fifth and sixth radial positions of the fiber probe illustrated in FIG. 8A, yield collected signals for the first subject 171 that contain larger than average fat absorbance features, which indicates that the fifth and sixth fiber rings of the example fiber bundle should not be used in the subsequent second data collection phase. Still in the first sample mapping phase, probing the tissue of the subject with photons from the fourth fiber ring yields a reduced signal for the first spectral marker and/or a larger relative signal for a second spectral marker related to the dermis 174, such as a protein absorbance band or an algorithmic/mathematical representation thereof. Hence, the data processing system 140 yields a result that the fifth and sixth radial fiber optic rings or distance of the fiber bundle 170 should not be used in the second data collection phase and that the fourth radial fiber optic ring or distance should be used in the second data collection phase. Subsequently, in the second data collection phase, data collection for analyte determination ensues using the first through fourth radial positions of the fiber bundle, which yields a larger signal-to-noise ratio for dermis constituents, such as glucose, compared to the use of all six radial positions of the fiber bundle.

In a second example, the first sample mapping phase of the previous example is repeated for the second subject 172. The first sample mapping phase indicates that for the second subject, the sixth radial illumination ring of the fiber bundle illustrated in FIG. 8A should not be used, but that the fourth and fifth radial illumination ring should be used.

In a third example, the first mapping phase determines positions on the skin where papillary dermis ridges are closest to the skin surface and positions on the skin where the papillary dermis valleys are furthest from the skin surface. In a subsequent data collection phase the incident light is optionally targeted at the papillary dermis valleys, such as greater than 50, 60, or 70 percent of the incident light is targeted at the papillary dermis valley and less than 30, 40, or 50 percent of the incident light is targeted at the papillary dermis ridge. The increased percentage of the incident light striking the papillary dermis valley increases the number of photons sampling the underlying dermis layer, where blood borne analytes reside, which increases the signal-to-noise ratio of collected data and lowers resultant errors in blood borne analyte property determination.

Generally, a particular subject is optionally probed in a sample mapping phase and results from the sample mapping phase are optionally used to configure analyzer parameters in a subsequent data collection phase. Optionally, the mapping phase and data collection phase occur within thirty seconds of each other. Optionally, the subject 170 does not move away from the sample interface 150 between the mapping phase and the data collection phase.

Further, generally each of the spatial and temporal methods yield information on pathlength, b, and/or a product of the molar absorptivity and pathlength, which is not achieved using a standard spectrometer.

In yet another embodiment, the sample interface tip 716 of the fiber optic bundle 710 includes optics that change the mean incident light angle of individual fibers of the fiber optic bundle 716 as they first hit the subject 170. For example, a first optic at the end of a fiber in the first ring 741 aims light away from the collection fiber optic 718; a second optic at the end of a fiber in the second ring 742 aims light nominally straight into the sample; and a third optic at the end of a fiber in the third ring 742 aims light toward the collection fiber 718. Generally, the mean direction of the incident light varies by greater than 5, 10, 15, 20, or 25 degrees.

Still yet another embodiment includes any combination and/or permutation of any of the analyzer and/or sensor elements described herein.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. An apparatus for noninvasively determining an analyte concentration at a sample site of a subject, comprising:
   a noninvasive analyzer, comprising:
      a source configured to provide photons;
      means for independently irradiating as a function of time each member of a set of mean radial distances from a center of the sample site of the subject with the photons, said means for independently irradiating comprising a vibration reduction system for maintaining an offset distance between said means for independently irradiating and a surface of the sample site;
         wherein a first member of said set of mean radial distances, comprises a first distance of less than two and a half millimeters and greater than six hundred micrometers,
         wherein a second member of said set of mean radial distances comprises a second distance of less than one millimeter and greater than one-quarter millimeter, and
         wherein a third member of said set of mean radial distances comprises a third distance of less than one-half millimeter; and
      a detector configured to sequentially detect the photons traversing through each member of said set of mean radial distances independently of remaining members of said set of mean radial distances, said analyzer configured to use the detected photons in determination of the analyte concentration.

2. The apparatus of claim 1, wherein said means for independently irradiating comprises:
   a fiber optic bundle, comprising a set of irradiation fiber optics configured at least three radial distances from at least one collection fiber optic; and
   means for sequentially irradiating each of: a first fiber, a second fiber, and a third fiber of said set of irradiation fiber optics with the photons.

3. The apparatus of claim 2, wherein said means for sequentially irradiating comprises:
   a mask element, said mask element configured to selectively mask individual groups of said fibers of said set of irradiation fiber optics from the photons from said source as a function of time.

4. The apparatus of claim 3, wherein said mask element is further configured to alter an axial cross-sectional area of a beam shape of the photons to each of:
   a first cross-sectional area when irradiating at the first distance of said set of mean radial distances,
   a second cross-sectional area when irradiating at the second distance of said set of mean radial distances, and
   a third cross-sectional area when irradiating at the third distance of said set of mean radial distances.

5. The apparatus of claim 3, wherein said analyzer further comprises:
   a fiber optic bundle comprising:
      a first irradiation fiber optic comprising a first axial cross-sectional area; and
      a second irradiation fiber optic comprising a second axial cross-sectional area, said second cross-sectional area at least twenty percent larger than said first cross-sectional area, both said first irradiation fiber optic and said second irradiation fiber optic configured to receive the photons,
   wherein said mask sequentially couples to said first irradiation fiber optic and said second irradiation fiber optic.

6. The apparatus of claim 5, wherein said fiber optic bundle further comprises:
   a sample light collection optic configured to optically connect to said detector, wherein said first fiber optic is disposed at a first physical separation distance from said sample light collection optic at an interface of the fiber optic bundle to the subject, and said second fiber optic is disposed at a second physical separation distance from said light collection optic at the interface, said second physical separation distance being at least twice said first physical separation distance.

7. The apparatus of claim 1, wherein said means for independently irradiating further comprises an optic configured to:

selectively target valleys of an epidermal ridge of the subject with a greater number of the photons compared to a lesser number of the photons delivered to the epidermal ridge.

8. The apparatus of claim 1, wherein the photons are transmited through a subject/analyzer interface at:
   the first distance, wherein the first distance correlates to a first mean maximum depth path into a subcutaneous fat layer of skin of the subject; and
   the third distance, wherein the third distance correlates to a second mean path maximum depth path through an epidermis layer of skin of the subject without penetrating to the subcutaneous fat layer of the skin of the subject.

9. A method for noninvasively determining an analyte concentration at a sample site of a subject, comprising the steps of:
   using a source of an analyzer to provide photons;
   guiding the photons with a photon transport system to a set of mean radial distances from a center of the sample site of the subject;
   maintaining an offset distance between the photon transport system and a surface of the sample site using a vibration reduction system;
      wherein a first member of said set of mean radial distances, comprises a first distance of less than two and a half millimeters and greater than six hundred micrometers,
      wherein a second member of said set of mean radial distances comprises a second distance of less than one millimeter and greater than one-half millimeter, and
   wherein a third member of said set of radial distances comprises a third distance of less than one-half millimeter; and
      sequentially detecting the photons traversing through each of said first member, said second member, and said third member of said set of mean radial distances independently of detection of the photons of remaining member distances of said first member, said second member, and said third member of said set of mean radial distances.

10. The method of claim 9, further comprising the step of:
   using a data processing system to determine a mean radial distance of the photons comprising a mean maximum depth penetrating into subcutaneous fat of the subject using the detected photons.

11. The method of claim 9, further comprising the steps of, during analysis of the subject:
   clipping an outer perimeter of a beam path of the photons to form a first axial cross-sectional area at a first location at a first point in time; and
   clipping an outer perimeter of the beam path to form a second axial cross-sectional area at the first location at a second point in time,
   wherein the first axial cross-sectional area is at least thirty percent larger than the second axial cross-sectional area.

12. The method of claim 9, further comprising the steps of, during analysis of the subject:
   providing a mask element, said mask element configured to selectively mask individual groups of fibers of said set of irradiation fiber optics from the photons from said source as a function of time;
   concentrating the photons to a first intensity per unit area at a first interface to an outer surface of skin of the subject during a first period of time using the mask element; and
   concentrating the photons to a second intensity per unit area at a second interface to the subject during a second period of time using the mask element,
   wherein the first intensity comprises at least fifty percent more photons per unit area than the second intensity.

* * * * *